(12) United States Patent
Tanaka et al.

(10) Patent No.: US 8,453,637 B2
(45) Date of Patent: Jun. 4, 2013

(54) PNEUMOSTOMA MANAGEMENT SYSTEM FOR TREATMENT OF CHRONIC OBSTRUCTIVE PULMONARY DISEASE

(75) Inventors: Don Tanaka, Saratoga, CA (US); Joshua P. Wiesman, Boston, MA (US); David C. Plough, Portola Valley, CA (US); Jeffrey C. Cerier, Franklin, MA (US); Richard A. Abraham, Reading, MA (US); Stephen C. Evans, Westford, MA (US); Gary L. Boseck, Belmont, CA (US)

(73) Assignee: Portaero, Inc., Cupertino, CA (US)

( * ) Notice: Subject to any disclaimer, the term of this patent is extended or adjusted under 35 U.S.C. 154(b) by 1010 days.

(21) Appl. No.: 12/388,447

(22) Filed: Feb. 18, 2009

(65) Prior Publication Data

US 2009/0205644 A1    Aug. 20, 2009

Related U.S. Application Data

(66) Substitute for application No. 61/151,581, filed on Feb. 11, 2009.

(60) Provisional application No. 61/029,830, filed on Feb. 19, 2008, provisional application No. 61/032,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009.

(51) Int. Cl.
*A61M 16/00*    (2006.01)
*A61M 5/00*    (2006.01)

(52) U.S. Cl.
USPC ............ 128/200.24; 128/202.27; 128/205.12; 128/205.19; 128/205.24; 604/45; 604/174; 604/175; 604/180; 604/304; 604/307; 604/386

(58) Field of Classification Search
USPC ............ 128/200.24, 200.25, 202.27, 205.12, 128/205.19, 205.24; 604/45, 174, 175, 180, 604/304, 307, 386
See application file for complete search history.

(56) References Cited

U.S. PATENT DOCUMENTS

| 733,152 A | 7/1903 | Chisholm |
|---|---|---|
| 953,922 A | 4/1910 | Rogers |

(Continued)

FOREIGN PATENT DOCUMENTS

| EP | 0260543 A1 | 3/1988 |
|---|---|---|
| EP | 1358904 | 5/2003 |

(Continued)

OTHER PUBLICATIONS

International Search Report for PCT/US2009/034374 dated Jun. 22, 2011, 7 pages.
Rendina et al., "Feasibility and safety of the airway bypass procedure for patients with emphysema", The Journal of Thoracic and Cardiovascular Surgery 2003; 125: 1294-1299.
Rockey, Edward E., "Tube Pneumonostomy for Thoracotomy Reject Crippling Bulbous Emphysema", New York State Journal of Medicine Mar. 1, 1973: 664-671.

(Continued)

*Primary Examiner* — Clinton T Ostrup
(74) *Attorney, Agent, or Firm* — Fliesler Meyer LLP

(57) ABSTRACT

A pneumostoma management system for maintaining the patency of a pneumostoma while controlling the flow of material through the pneumostoma. The pneumostoma management system includes a two-part pneumostoma management device and associated insertion and removal tools. The pneumostoma management device includes a pneumostoma vent and a chest mount for positioning and securing the vent into a pneumostoma. The pneumostoma vent includes a hydrophobic filter and/or a one-way valve.

21 Claims, 19 Drawing Sheets

U.S. PATENT DOCUMENTS

| | | | |
|---|---|---|---|
| 2,206,687 A | 7/1940 | Bloomheart | |
| 2,867,213 A | 1/1959 | Thomas, Jr. | |
| 2,873,742 A | 2/1959 | Shelden | |
| 2,991,787 A | 7/1961 | Shelden et al. | |
| 3,253,594 A | 5/1966 | Matthews et al. | |
| 3,384,087 A | 5/1968 | Brummelkamp | |
| 3,463,159 A | 8/1969 | Heimlich | |
| 3,511,243 A | 5/1970 | Toy | |
| 3,556,103 A | 1/1971 | Calhoun et al. | |
| 3,638,649 A | 2/1972 | Ersek | |
| 3,682,166 A | 8/1972 | Jacobs | |
| 3,688,773 A | 9/1972 | Weiss | |
| 3,707,146 A | 12/1972 | Cook et al. | |
| 3,766,920 A | 10/1973 | Greene | |
| 3,777,757 A | 12/1973 | Gray et al. | |
| 3,788,326 A | 1/1974 | Jacobs | |
| 3,817,250 A | 6/1974 | Weiss et al. | |
| 3,908,704 A | 9/1975 | Clement et al. | |
| 3,916,903 A | 11/1975 | Pozzi | |
| 3,924,637 A * | 12/1975 | Swanson | 128/207.16 |
| 4,153,058 A | 5/1979 | Nehme | |
| 4,291,694 A | 9/1981 | Chai | |
| 4,439,189 A | 3/1984 | Sargeant et al. | |
| 4,465,062 A | 8/1984 | Versaggi et al. | |
| 4,502,482 A | 3/1985 | DeLuccia et al. | |
| 4,583,977 A | 4/1986 | Shishov et al. | |
| 4,664,660 A | 5/1987 | Goldberg et al. | |
| 4,799,494 A | 1/1989 | Wang | |
| 4,813,929 A | 3/1989 | Semrad | |
| 4,826,495 A | 5/1989 | Petersen | |
| 4,828,553 A | 5/1989 | Nielsen | |
| 4,869,717 A | 9/1989 | Adair | |
| 4,872,869 A | 10/1989 | Johns | |
| 4,889,534 A | 12/1989 | Mohiuddin et al. | |
| 4,931,045 A | 6/1990 | Steer | |
| 4,944,724 A | 7/1990 | Goldberg et al. | |
| 4,959,054 A | 9/1990 | Heimke et al. | |
| 4,976,688 A | 12/1990 | Rosenblum | |
| 5,004,456 A | 4/1991 | Botterbusch et al. | |
| 5,060,645 A | 10/1991 | Russell | |
| 5,078,689 A | 1/1992 | Keller | |
| 5,137,509 A | 8/1992 | Freitas | |
| 5,139,485 A | 8/1992 | Smith et al. | |
| 5,218,957 A | 6/1993 | Strickland | |
| 5,230,332 A | 7/1993 | Strickland | |
| 5,230,350 A | 7/1993 | Fentress | |
| 5,261,708 A | 11/1993 | Steer | |
| 5,263,939 A | 11/1993 | Wortrich | |
| 5,312,331 A | 5/1994 | Knoepfler | |
| 5,315,992 A | 5/1994 | Dalton | |
| 5,318,523 A | 6/1994 | Lu | |
| 5,336,206 A | 8/1994 | Shichman | |
| 5,354,283 A | 10/1994 | Bark et al. | |
| 5,356,386 A | 10/1994 | Goldberg et al. | |
| 5,366,478 A | 11/1994 | Brinkerhoff et al. | |
| 5,370,625 A | 12/1994 | Shichman | |
| 5,376,376 A | 12/1994 | Li | |
| 5,389,077 A | 2/1995 | Melinyshyn et al. | |
| 5,401,262 A | 3/1995 | Karwoski et al. | |
| 5,403,264 A | 4/1995 | Wohlers et al. | |
| 5,431,633 A | 7/1995 | Fury | |
| 5,478,333 A | 12/1995 | Asherman, Jr. | |
| 5,484,401 A | 1/1996 | Rodriguez et al. | |
| 5,487,382 A * | 1/1996 | Bezicot | 128/207.14 |
| 5,496,297 A | 3/1996 | Olsen | |
| 5,501,677 A | 3/1996 | Jensen | |
| 5,501,678 A | 3/1996 | Olsen | |
| 5,588,424 A | 12/1996 | Insler et al. | |
| 5,616,131 A | 4/1997 | Sauer et al. | |
| 5,660,175 A | 8/1997 | Dayal | |
| 5,662,629 A | 9/1997 | Steer et al. | |
| 5,728,066 A | 3/1998 | Daneshvar | |
| 5,730,735 A | 3/1998 | Holmberg et al. | |
| 5,738,661 A | 4/1998 | Larice | |
| 5,807,341 A | 9/1998 | Heim | |
| 5,830,200 A | 11/1998 | Steer et al. | |
| 5,843,053 A | 12/1998 | Steer | |
| 5,897,531 A | 4/1999 | Amirana | |
| 5,931,821 A | 8/1999 | Weilbacher et al. | |
| 5,954,636 A | 9/1999 | Schwartz et al. | |
| 5,971,962 A | 10/1999 | Kojima et al. | |
| 5,972,026 A | 10/1999 | Laufer et al. | |
| 6,056,744 A | 5/2000 | Edwards | |
| 6,059,816 A | 5/2000 | Moenning | |
| 6,083,255 A | 7/2000 | Laufer et al. | |
| 6,174,323 B1 | 1/2001 | Biggs et al. | |
| 6,197,010 B1 | 3/2001 | Leise, Jr. et al. | |
| 6,200,333 B1 | 3/2001 | Laufer | |
| 6,258,100 B1 | 7/2001 | Alferness et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,293,930 B1 | 9/2001 | Brunsgaard et al. | |
| 6,293,951 B1 | 9/2001 | Alferness et al. | |
| 6,299,633 B1 | 10/2001 | Laufer | |
| 6,322,536 B1 | 11/2001 | Rosengart et al. | |
| 6,328,689 B1 | 12/2001 | Gonzalez et al. | |
| 6,330,882 B1 | 12/2001 | French | |
| 6,334,441 B1 | 1/2002 | Zowtiak et al. | |
| 6,358,269 B1 | 3/2002 | Aye | |
| 6,398,775 B1 | 6/2002 | Perkins et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,432,100 B1 | 8/2002 | Affeld | |
| 6,443,156 B1 | 9/2002 | Niklason et al. | |
| 6,468,292 B1 | 10/2002 | Mollenauer et al. | |
| 6,485,407 B2 | 11/2002 | Alferness et al. | |
| 6,488,673 B1 | 12/2002 | Laufer et al. | |
| 6,491,706 B1 | 12/2002 | Alferness et al. | |
| 6,514,290 B1 | 2/2003 | Loomas | |
| 6,517,519 B1 | 2/2003 | Rosen et al. | |
| 6,520,183 B2 | 2/2003 | Amar | |
| 6,527,761 B1 | 3/2003 | Soltesz et al. | |
| 6,550,475 B1 | 4/2003 | Oldfield | |
| 6,569,121 B1 | 5/2003 | Purow et al. | |
| 6,569,166 B2 | 5/2003 | Gonzalez | |
| 6,585,639 B1 | 7/2003 | Kotmel et al. | |
| 6,589,161 B2 | 7/2003 | Corcoran | |
| 6,592,594 B2 | 7/2003 | Rimbaugh et al. | |
| 6,599,311 B1 | 7/2003 | Biggs et al. | |
| 6,609,521 B1 | 8/2003 | Belani et al. | |
| 6,629,951 B2 | 10/2003 | Laufer et al. | |
| 6,632,239 B2 | 10/2003 | Snyder et al. | |
| 6,632,243 B1 | 10/2003 | Zadno-Azizi et al. | |
| 6,634,360 B1 | 10/2003 | Flodin | |
| 6,634,363 B1 | 10/2003 | Danek et al. | |
| 6,638,253 B2 | 10/2003 | Breznock | |
| 6,653,525 B2 | 11/2003 | Ingenito et al. | |
| 6,659,961 B2 | 12/2003 | Robinson | |
| 6,679,264 B1 | 1/2004 | Deem et al. | |
| 6,682,506 B1 | 1/2004 | Navarro | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,712,812 B2 | 3/2004 | Roschak et al. | |
| 6,736,797 B1 | 5/2004 | Larsen et al. | |
| 6,749,606 B2 | 6/2004 | Keast et al. | |
| 6,770,063 B2 | 8/2004 | Goldberg et al. | |
| 6,770,070 B1 | 8/2004 | Balbierz | |
| 6,790,172 B2 | 9/2004 | Alferness et al. | |
| 6,827,086 B2 | 12/2004 | Shuman | |
| 6,837,906 B2 | 1/2005 | Ginn | |
| 6,840,243 B2 | 1/2005 | Deem et al. | |
| 6,843,767 B2 | 1/2005 | Corcoran et al. | |
| 6,846,292 B2 | 1/2005 | Bakry | |
| 6,849,061 B2 | 2/2005 | Wagner | |
| 6,852,108 B2 | 2/2005 | Barry et al. | |
| 6,860,847 B2 | 3/2005 | Alferness et al. | |
| 6,878,141 B1 | 4/2005 | Perkins et al. | |
| 6,886,558 B2 | 5/2005 | Tanaka | |
| 6,901,927 B2 | 6/2005 | Deem et al. | |
| 6,904,909 B2 | 6/2005 | Andreas et al. | |
| 6,905,518 B2 | 6/2005 | Ginn | |
| 6,916,310 B2 | 7/2005 | Sommerich | |

| Patent/Publication | Date | Inventor |
|---|---|---|
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,377,278 B2 | 5/2008 | Tanaka |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca'et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0079838 A1 | 4/2006 | Walker et al. |
| 2006/0095002 A1 | 5/2006 | Soltesz et al. |

| | | | |
|---|---|---|---|
| 2006/0107961 A1 | 5/2006 | Tanaka | |
| 2006/0116749 A1 | 6/2006 | Willink et al. | |
| 2006/0118125 A1 | 6/2006 | Tanaka | |
| 2006/0118126 A1 | 6/2006 | Tanaka | |
| 2006/0124126 A1* | 6/2006 | Tanaka | 128/200.26 |
| 2006/0130830 A1 | 6/2006 | Barry | |
| 2006/0135947 A1 | 6/2006 | Soltesz et al. | |
| 2006/0135984 A1 | 6/2006 | Kramer et al. | |
| 2006/0142672 A1 | 6/2006 | Keast et al. | |
| 2006/0161233 A1 | 7/2006 | Barry et al. | |
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |
| 2007/0299424 A1 | 12/2007 | Cumming et al. | |
| 2008/0281151 A1 | 11/2008 | Chang et al. | |
| 2008/0281295 A1 | 11/2008 | Chang et al. | |
| 2008/0281433 A1 | 11/2008 | Chang et al. | |
| 2008/0283065 A1 | 11/2008 | Chang et al. | |
| 2008/0287878 A1 | 11/2008 | Tanaka | |
| 2008/0287973 A1 | 11/2008 | Aster et al. | |
| 2008/0295829 A1 | 12/2008 | Evens | |
| 2009/0205641 A1 | 8/2009 | Tanaka | |
| 2009/0205643 A1 | 8/2009 | Tanaka et al. | |
| 2009/0205644 A1 | 8/2009 | Tanaka et al. | |
| 2009/0205645 A1 | 8/2009 | Tanaka et al. | |
| 2009/0205646 A1 | 8/2009 | Tanaka et al. | |
| 2009/0205647 A1 | 8/2009 | Plough et al. | |
| 2009/0205648 A1 | 8/2009 | Tanaka et al. | |
| 2009/0205649 A1 | 8/2009 | Tanaka et al. | |
| 2009/0205650 A1 | 8/2009 | Tanaka et al. | |
| 2009/0205651 A1 | 8/2009 | Tanaka et al. | |
| 2009/0205658 A1 | 8/2009 | Tanaka et al. | |
| 2009/0205665 A1 | 8/2009 | Tanaka et al. | |
| 2009/0209856 A1 | 8/2009 | Tanaka et al. | |
| 2009/0209906 A1 | 8/2009 | Tanaka et al. | |
| 2009/0209909 A1 | 8/2009 | Tanaka et al. | |
| 2009/0209917 A1 | 8/2009 | Tanaka et al. | |
| 2009/0209924 A1 | 8/2009 | Tanaka | |
| 2009/0209936 A1 | 8/2009 | Tanaka et al. | |
| 2009/0209970 A1 | 8/2009 | Tanaka et al. | |
| 2009/0209971 A1 | 8/2009 | Tanaka et al. | |

FOREIGN PATENT DOCUMENTS

| | | |
|---|---|---|
| EP | 1658867 | 5/2006 |
| EP | 1815821 | 8/2007 |
| EP | 2242527 | 10/2010 |
| JP | 62-2028747 U | 6/1986 |
| JP | 2000-197706 | 7/2000 |
| JP | 2000197706 | 7/2000 |
| RU | 2192185 | 10/2002 |
| WO | WO 96/39960 | 12/1996 |
| WO | WO 99/66975 | 12/1999 |
| WO | WO 00/76577 A1 | 12/2000 |
| WO | WO 01/45568 A1 | 6/2001 |
| WO | WO 02/04054 | 1/2002 |
| WO | WO2005070480 | 8/2005 |

OTHER PUBLICATIONS

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e...> May 2, 2007.

Shah, Pallav, "Surgical and Non-surgical volume Reduction for COPD", Presented at the Clinical Consensus on COPD, Mar. 2-3, 2007, Novotel London West, pp. 1-44.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woolcock et al., "Mechanical factors influencing collateral ventilation in human, dog, and pig lungs", Journal of Applied Physiology 1971, 30: 99-115.

Woodring et al., "Pneumothorax ex vacuo", Chest 1996, 110: 1102-1124.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.
International Search Report for PCT/US2009/034322 dated Oct. 5, 2009; 14 pages.
International Search Report for PCT/US2009/034406 dated Dec. 2, 2009; 16 pages.
Moore et al., "Unilateral Extrapulmonary Airway Bypass in Advanced Emphysema", The Annals of Thoracic Surgery 2010; 89:899-906.
International Search Report for PCT/US2009/034322 dated Jun. 6, 2011, 7 pages.
Extended European Search Report dated Jun. 22, 2011 for PCT/US2009034374, 7 pages.
Extended European Search Report dated Jun. 15, 2011 for PCT/US2009034322, 7 pages.
Extended European Search Report dated Sep. 16, 2011 for PCT/US2009034380, 8 pages.
Aljuri et al., "Validation and pilot clinical study of a new bronchoscopic method to measure collateral ventilation before endobronchial lung volume reduction", J Appl Physio 106: 774-783, 2009.
Al-Salem et al., "Computed tomography-guided percutaneous needle aspiration of lung abscesses in neonates and children", Pediatr Surg Int (1997) 12: 417-419, copyright Springer-Verlag 1997.
Ball, Jr et al., "Percutaneous Drainage of Chest Abscesses in Children", Radiology 1989; 171: 431-434.
Becker et al., "Lung Volumes before and after Lung Volume Reduction Surgery: Quantitative CT Analysis", Am J Respir Crit Care Med 1998; 157: 1593-1599.
Brenner et al., "Innovative Approaches to Lung Volume Reduction for Emphysema", Chest 2004; 126: 238-248.
Brutinel et al., "A two-year experience with the neodymium-YAG laser in endobronchial obstruction", Chest 1987; 91: 159-165.
Celli et al. "Standards for the diagnosis and treatment of patients with COPD: a summary of the ATS/ERS position paper", European Respiratory Journal 2004; 23; 932-946.
Cetti et al., "Collateral ventilation", Thorax 2006; 61: 371-373.
Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System, (2003).
Choong et al., "Feasibility and safety of airway bypass stent placement and influence of topical mitomycin C on stent patency", The Journal of Thoracic and Cardiovascular Surgery 2005; 129: 632-638.
Choong et al., "Transpleural ventilation of explanted human lungs", Thorax 2007; 62: 623-630; originally published online Apr. 5, 2007.
Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.
Dumon, J. F., "A Dedicated Tracheobronchial Stent", Chest 1990; 97: 328-332.
Eloesser, "An Operation for Tuberculous Empyema", Chest 1935; 1: 8-23.
Fein, Alan M, "Lung Volume Reduction Surgery: Answering the Crucial Questions", Chest 1998; 113: 277-282.
Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.
Fessler, Henry E., "Collateral Ventilation, the Bane of Bronchoscopic Volume Reduction", Am J Respir Crit Care Med 2005; 171: 423-425.
Frawley et al., "Airway Pressure Release Ventilation: Theory and Practice", AACN Clinical Issues 2001; vol. 12, No. 2: 234-246.
Freitag et al., "Theoretical and experimental basis for the development of a dynamic airway stent", European Respiratory Journal 1994; 7: 2038-2045.
Ghaye et al., "Imaging guided thoracic interventions", European Respiratory Journal 2001; 17: 507-528.
Golding et al., "External drainage of large bullae in severe generalized emphysema", Journal of Thoracic and Cardiovascular Surgery Jun. 1968; vol. 55, No. 6: 891-894.
Goldstraw et al., "The Surgical Treatment of Emphysema: The Brompton Approach", Chest Surgery Clinics of North America Nov. 1995; vol. 5, No. 4: 777-797.
Habashi, Nader M., "Other approaches to open-lung ventilation: Airway pressure release ventilation", Crit Care Med 2005, vol. 33, No. 3 (Suppl): S228-S240.
Harada et al., "Re-expansion of Refractory Atelectasis Using a Bronchofiberscope with a Balloon Cuff", Chest 1983; 84: 725-728.
Head et al., "Intracavitary Suction (Monaldi) in the Treatment of Emphysematous Bullae and Blebs", Journal of Thoracic Surgery Dec. 1949; vol. 18, No. 6: 761-776.
Heimlich, Henry J., "Respiratory Rehabilitation with Transtracheal Oxygen System", Ann Otol Rhinol Laryngol Nov./Dec. 1982; 91: 643-647.
Hogg et al., "Chronic obstructive pulmonary disease c2: Pathology and biochemistry of emphysema", Thorax 2002; 57: 830-834.
Hogg et al., "The Resistance of Collateral Channels in Excised Human Lungs", Journal of Clinical Investigation 1969; 48: 421-431.
Joannette, Albert, "Drainage of Tuberculous Cavities by Aspiration (Monaldi Method)", The Canadian Medical Association Journal Jan. 1941; 46-48.
Korpela et al., "Bioabsorbable Self-reinforced Poly-L-Lactide, Metallic, and Silicone Stents in the Management of Experimental Tracheal Stenosis", Chest 1999; 115: 490-495.
Lausberg et al., "Bronchial Fenestration Improves Expiratory Flow in Emphysematous Human Lungs", Annals of Thoracic Surgery 2003; 75: 393-398.
Lorenzo et al., "Lung Abscesses in Children: Diagnostic and Therapeutic Needle Aspiration", Radiology Oct. 1985; 157: 79-80.
MacArthur et al., "Intracavity suction and drainage in the treatment of emphysematous bullae", Thorax 1977; 32: 668-672.
Macklem, Peter T., "Collateral Ventilation", The New England Journal of Medicine Jan. 5, 1978; 298(1): 49-50.
Matson et al., "Evaluation of Various Surgical Procedures in the Treatment of Pulmonary Tuberculosis", Chest 1946; 12: 40-47.
McCoy, Robert, "Oxygen-Conserving Techniques and Devices", Respiratory Care Jan. 2000, vol. 45, No. 1: 95-104.
Meyers et al., "Chronic obstructive pulmonary disease 10: Bullectomy, lung volume reduction surgery, and transplantation for patients with chronic obstructive pulmonary disease", Thorax 2003; 58: 634-638.
Mineo et al., "Awake Nonresectional Lung Volume Reduction Surgery", Annals of Surgery 2006; 243: 131-136.
Monaldi, V., "Endocavitary Aspiration: Its Practical Application", Tubercle 1947: 223-228.
Monaldi, V., "Endocavitary Aspiration in the Treatment of Lung Abscess", Chest 1956; 29: 193-201.
Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.
U.S. Department of Health and Human Services; National Institutes of Health National Heart, Lung, and Blood Institute; "Chronic Obstructive Pulmonary Disease", NIH Publication No. 03-5229 Mar. 2003: 1-6.
Parker et al., "Percutaneous small bore catheter drainage in the management of lung abscesses", Chest 1987; 92: 213-218.
Petty, Thomas L., "The history of COPD", International Journal of COPD 2006; 1(1): 3-14.
Polkey, M. J., "Surgical procedures in emphysema: any impact on dynamic hyperinflation?" European Respiratory Review 2006; 15(100): 96-98.
Polkey, M. J., "Bronchoscopic lung volume reduction" European Respiratory Review 2006; 15(100): 99-103.

* cited by examiner

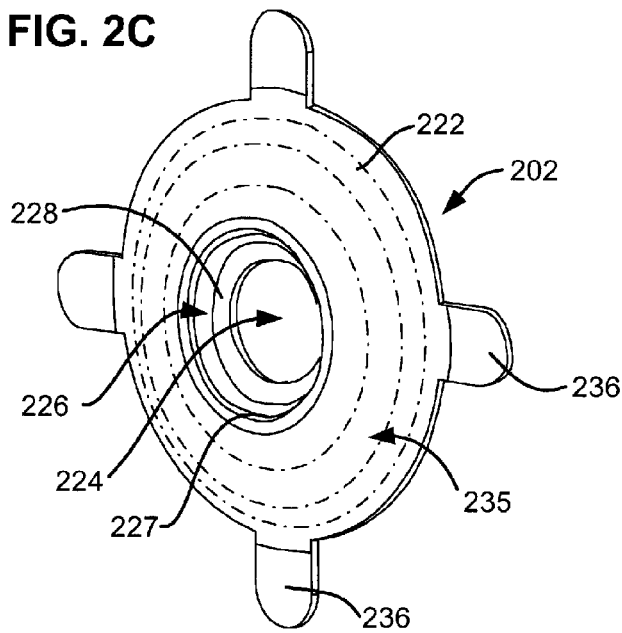
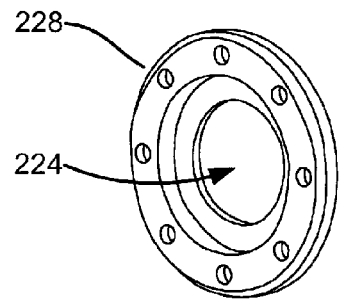
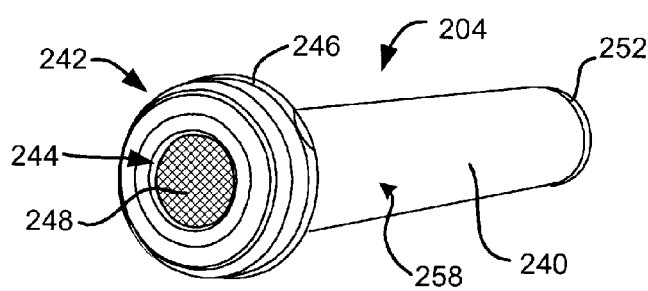
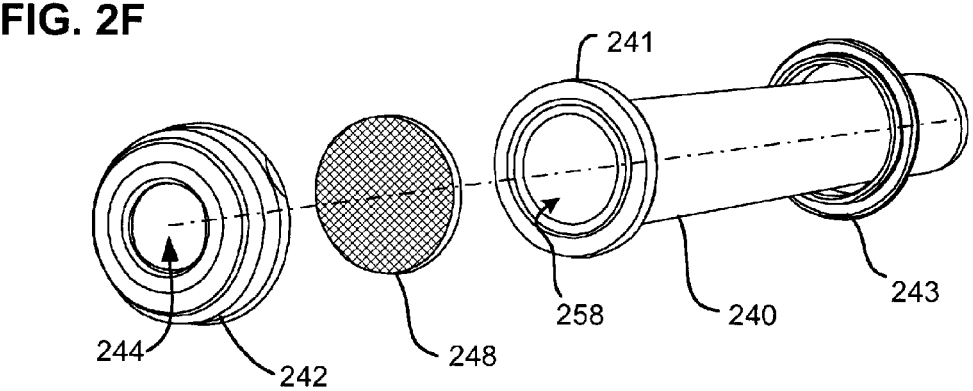

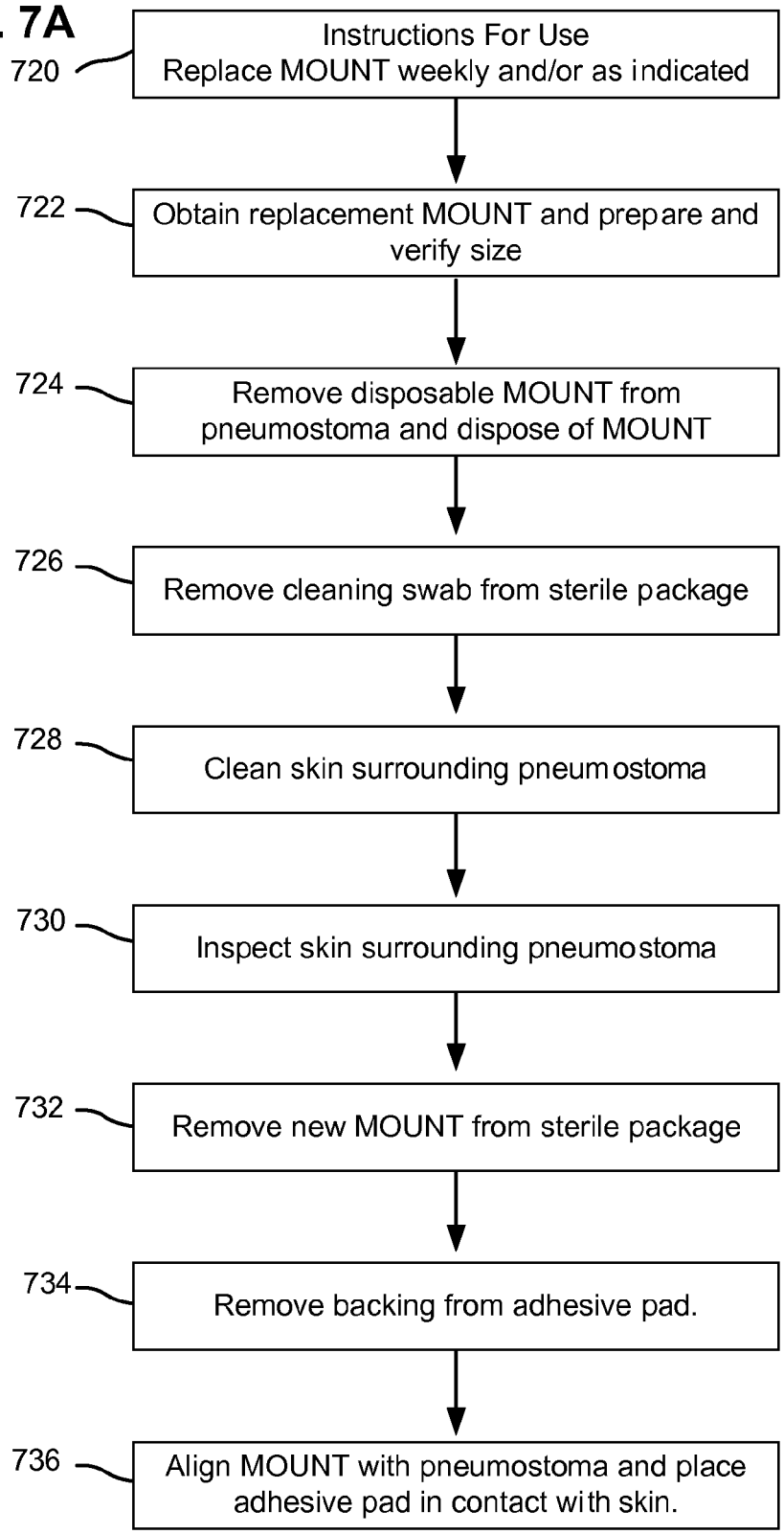

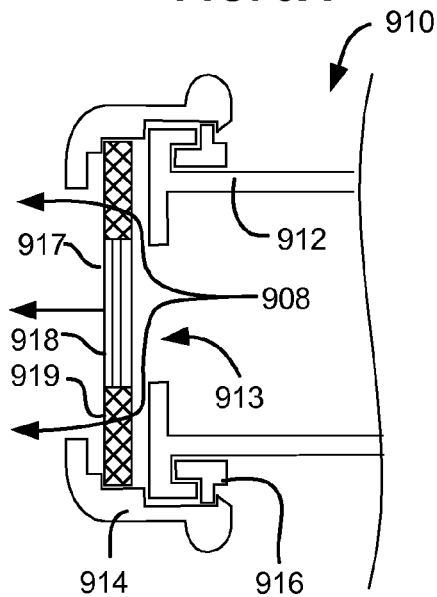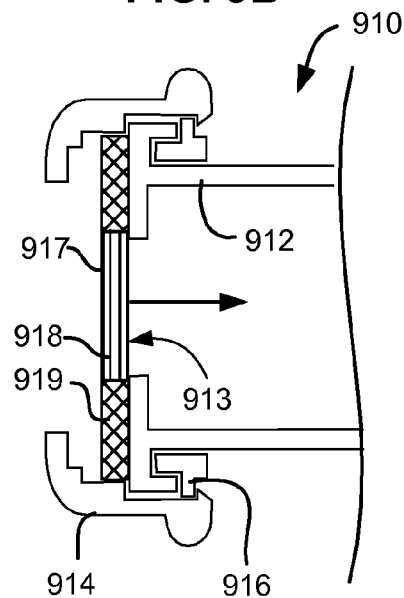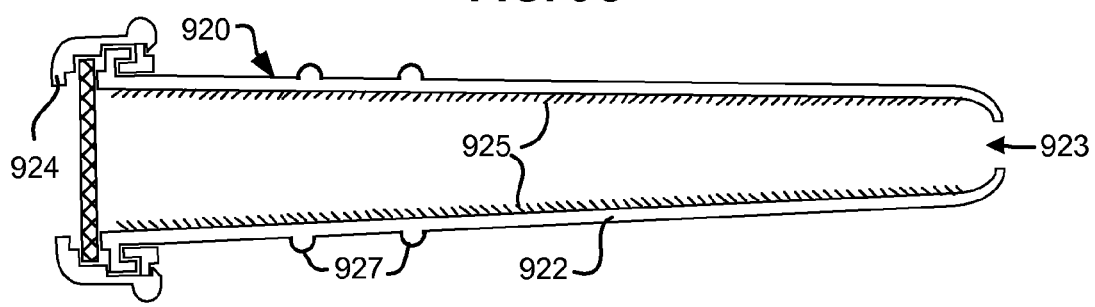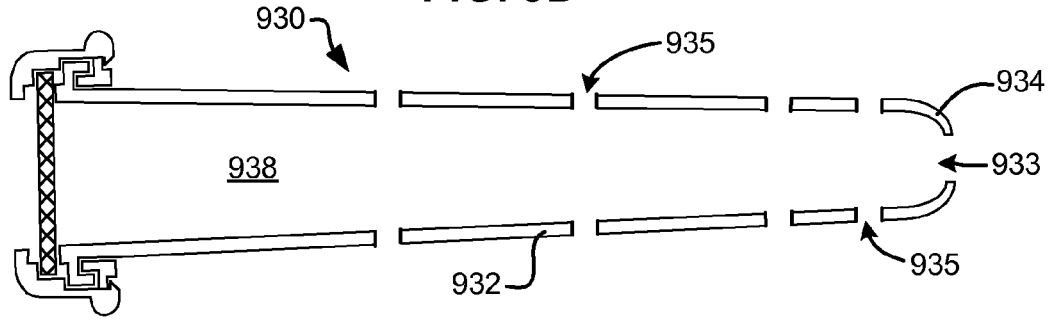

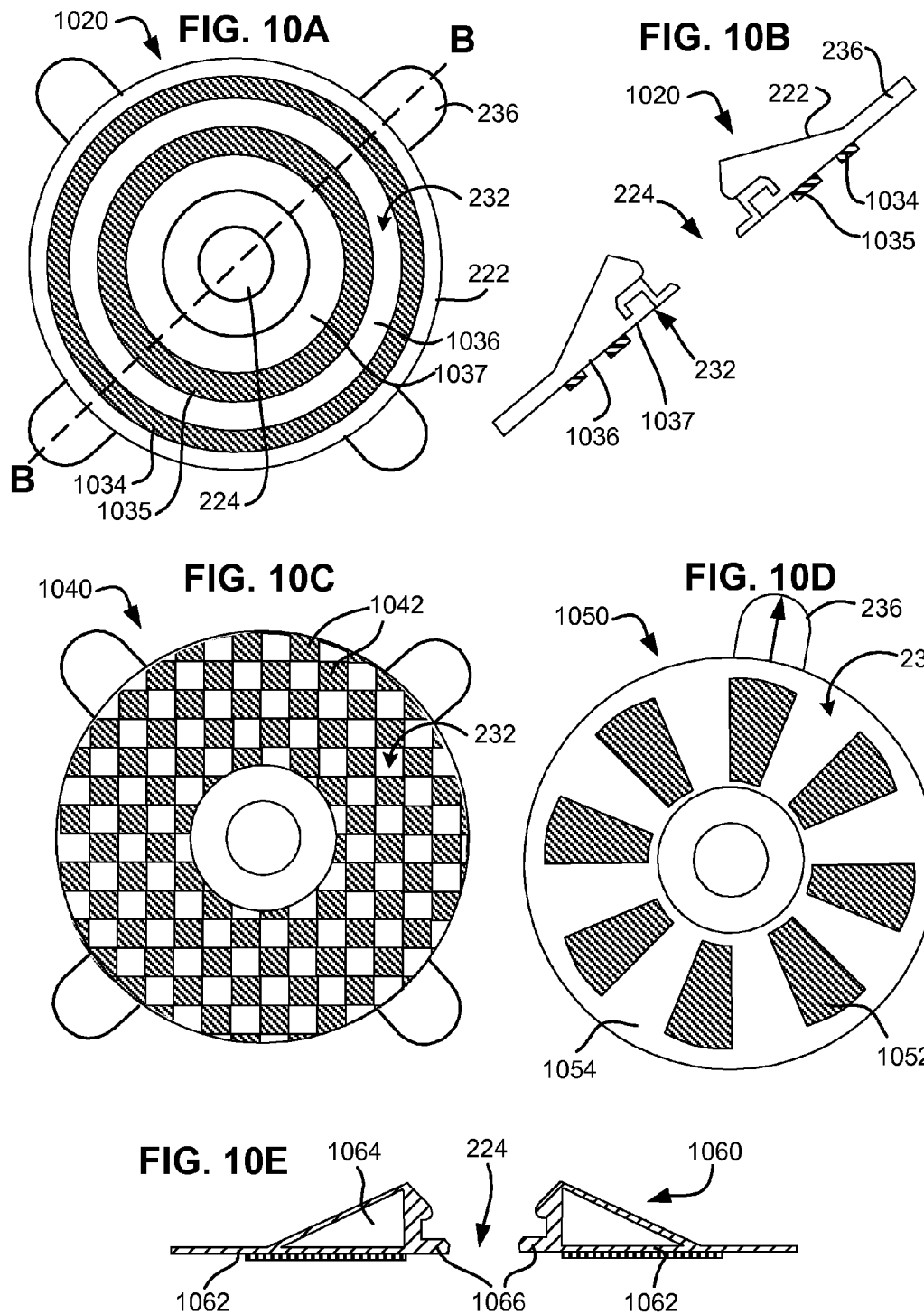

PNEUMOSTOMA MANAGEMENT SYSTEM FOR TREATMENT OF CHRONIC OBSTRUCTIVE PULMONARY DISEASE

CLAIM TO PRIORITY

This application claims priority to all of the following applications including: U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, now U.S. Pat. No. 7,909,803, issued Mar. 22, 2011, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446, filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,460, filed Feb. 18, 2009, entitled "PNEUOMOSTOMA MANAGEMENT SYSTEM HAVING A COSMETIC AND/OR PROTECTIVE COVER";

U.S. patent application Ser. No. 12/388,455, filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, now U.S. Pat. No. 8,348,906, issued Jan. 8, 2013, entitled "ASPIRATOR FOR PNEUMOSTOMA MANAGEMENT";

U.S. patent application Ser. No. 12/388,462, filed Feb. 18, 2009, now U.S. Pat. No. 7,927,324, issued Apr. 19, 2011, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,453, filed Feb. 18, 2009, now U.S. Pat. No. 8,252,003, issued Aug. 28, 2012, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, now U.S. Pat. No. 8,347,880, issued Jan. 8, 2013, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, now U.S. Pat. No. 8,365,722, issued Feb. 5, 2013, entitled "MULTI-LAYER PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE"; and U.S. patent application Ser. No. 12/388,470, filed Feb. 18, 2009, now U.S. Pat. No. 8,021,320, issued Sep. 20, 2011, entitled "SELF-SEALING DEVICE AND METHOD FOR DELIVERY OF A THERAPEUTIC AGENT THROUGH A PNEUMOSTOMA".

All of the afore-mentioned are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments, for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The artificial aperture into the lung through the chest is referred to herein as a pneumostoma. A pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing a portion of the lung or sealing off a portion of the lung.

In accordance with one embodiment, the present invention provides a two piece pneumostoma management system which includes two component pneumostoma management device having a partially-implantable pneumostoma vent and a chest mount. The partially-implantable pneumostoma vent is placed into a pneumostoma through the chest mount to maintain the patency of the pneumostoma, prevent the entry of foreign substances into the lung, control air flow through the pneumostoma and collect any materials that may exit the lung.

In accordance with one embodiment, the present invention provides a two piece pneumostoma management system which includes a partially-implantable pneumostoma vent and a chest mount. The partially-implantable pneumostoma vent is placed into a pneumostoma through an aperture in the chest mount. The partially-implantable pneumostoma management device is designed such that every component is larger than the aperture and, thus, cannot enter the pneumostoma.

In accordance with one embodiment, the present invention provides a two piece pneumostoma management system which includes a partially-implantable pneumostoma vent and a chest mount. The partially-implantable pneumostoma vent is placed into a pneumostoma through an aperture in the chest mount. Insertion and removal tools are provided for inserting the partially-implantable pneumostoma vent into the chest mount and removing it from the chest mount.

In accordance with one embodiment, the present invention provides a two piece pneumostoma management system which includes a partially-implantable pneumostoma vent and a chest mount. An insertion tool is used to position the partially-implantable pneumostoma vent into a pneumostoma through an aperture in the chest mount. The removal tool is designed such that it does not release the pneumostoma management device after extraction thereby protecting the non-sterile device from reuse.

In accordance with one embodiment, the present invention provides a two piece pneumostoma management system which includes a partially-implantable pneumostoma vent and a chest mount. The partially-implantable pneumostoma vent is placed into a pneumostoma through an aperture in the chest mount. The chest mount is secured to the skin of the patient and is replaced every two days to one week. The pneumostoma vent is replaced daily or when necessary.

In accordance with another embodiment of the present invention, a method is provided for using the disclosed pneumostoma management system to maintain the patency of the pneumostoma, prevent the entry of foreign substances into the lung, control air flow through the pneumostoma and collect any materials that may exit the lung.

In accordance with another embodiment of the invention, methods are provided utilizing insertion and removal tools to insert and remove components of the pneumostoma management system in a controlled and sterile manner.

Thus, various systems, components and methods are provided for managing a pneumostoma and thereby treating COPD. Other objects, features and advantages of the invention will be apparent from the drawings and the detailed description to follow.

BRIEF DESCRIPTION OF THE DRAWINGS

The above and further features, advantages and benefits of the present invention will be apparent upon consideration of the present description taken in conjunction with the accompanying drawings.

FIG. 1C shows a detailed sectional view of a pneumostoma.

FIG. 2C shows a perspective view of the mounting flange of FIG. 2A.

FIG. 2D shows a perspective view of the aperture plate of the flange of FIG. 2C.

FIG. 2E shows a perspective view of the pneumostoma vent of FIG. 2A.

FIG. 2F shows an exploded perspective view of the pneumostoma vent of FIG. 2E.

FIGS. 7A and 7B show instruction for using a pneumostoma management system in accordance with an embodiment of the present invention.

FIGS. 9A-9D show alternative pneumostoma vent configurations for pneumostoma management systems according to embodiments of the present invention.

FIGS. 10A-10E show alternative chest mount configurations for pneumostoma management systems according to embodiments of the present invention.

DETAILED DESCRIPTION OF THE INVENTION

Figure 1A:
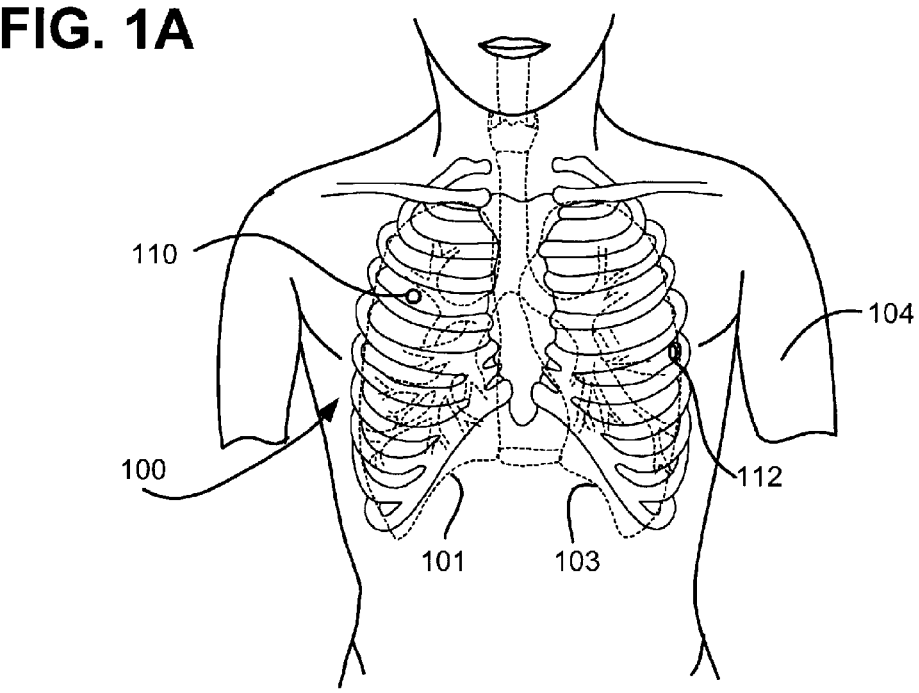
FIG. 1A shows the chest of a patient indicating alternative locations for a pneumostoma that may be managed using the device and methods of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Formation and Anatomy

FIG. 1A shows the chest of a patient indicating alternative locations for creating a pneumostoma that may be managed using the system and methods of the present invention. A first pneumostoma 110 is shown on the front of the chest 100 over the right lung 101 (shown in dashed lines). The pneumostoma is preferably positioned over the third intercostal space on the mid-clavicular line. Thus, the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A, a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis. Methods for forming the channel, opening, anastomosis and pleurodesis are disclosed in Applicants' pending and issued patents and applications including U.S. patent application Ser. No. 10/881,408, now U.S. Pat. No. 7,682,332, entitled "Methods and Devices to Accelerate Wound Healing in Thoracic Anastomosis Applications," U.S. patent application Ser. No. 12/030,006, now U.S. Pat. No. 8,062,315, entitled "Variable Parietal/Visceral Pleural Coupling," and U.S. Provisional Application No. 61/038,371 entitled "Surgical Procedure And Instrument To Create A Pneumostoma And Treat Chronic Obstructive Pulmonary Disease" which are incorporated herein by reference in their entireties.

Figure 1B:
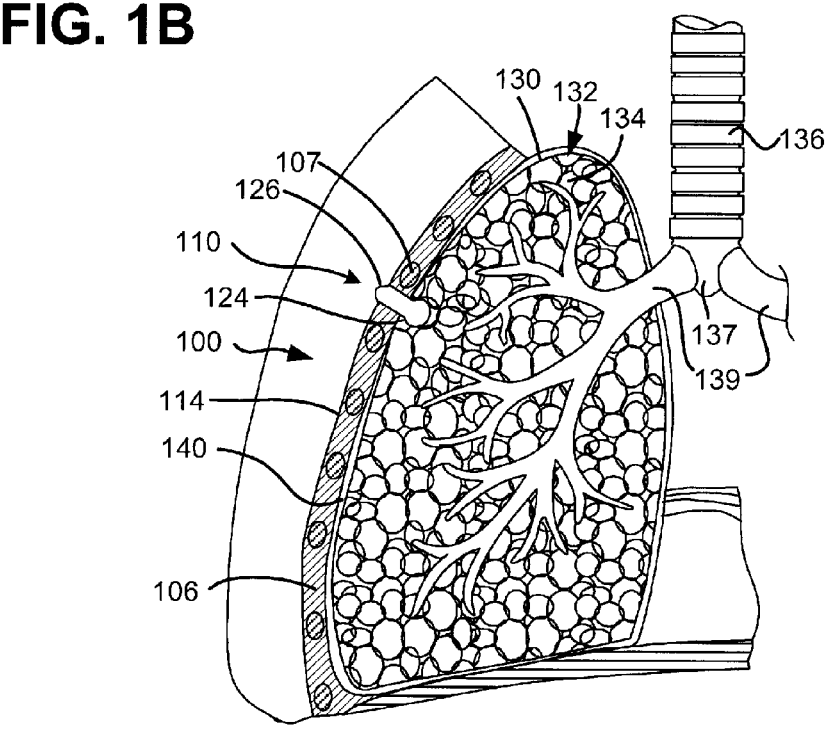
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 139. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124, the pleural membranes are fused and/or adhered to one another eliminating the space between the pleural membranes in that region.

An important feature of the pneumostoma is the seal or adhesion surrounding the channel 120 where it enters the lung 130 which may comprise a pleurodesis 124. A pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the pleurodesis 124 is preferably localized to the region surrounding the channel 120. The pleurodesis 124 surrounding the channel 120 prevents air from entering the pleural cavity 140. If air is permitted to enter pleural cavity 140, a pneumothorax will result and the lung may collapse.

Pleurodesis 124 can be created between the visceral pleura of the lung and the inner wall of the thoracic cavity using chemical methods including introducing into the pleural space irritants such as antibiotics (e.g. Doxycycline or Quinacrine), antivirals (e.g. iodopovidone or silver nitrate), anticancer drugs (e.g. Bleomycin, Mitoxantrone or Cisplatin), cytokines (e.g. interferon alpha-2β and Transforming growth factor-β); pyrogens (e.g. *Corynebacterium parvum, Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedure is called dry abrasion pleurodesis. A pleurodesis may also be created using radiotherapy methods, including radioactive gold or external radiation. These methods cause an inflammatory response and/or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop into pleurodesis over time. A range of biocompatible glues are available that may be used on the lung, including light-activatable glues, fibrin glues, cyanoacrylates and two part polymerizing glues. Applicants' copending U.S. patent application Ser. No. 12/030,006, now U.S. Pat. No. 8,062,315, entitled "VARIABLE PARIETAL/VISCERAL PLEURAL COUPLING" discloses methods such as pleurodesis for coupling a channel through the chest wall to the inner volume of the lung without causing a pneumothorax and is incorporated herein by reference for all purposes.

When formed, pneumostoma 110 provides an extra pathway for exhaled air to exit the lung 130 reducing residual volume and intra-thoracic pressure without the air passing through the major natural airways such as the bronchi 139 and trachea 136. Collateral ventilation is particularly prevalent in an emphysemous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110, thus, makes use of collateral ventilation to collect air in cavity 122 and vent the air outside the body via channel 120 reducing residual volume and intra-thoracic pressure and bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. Pneumostoma 110 thus achieves many of the advantages sought by lung volume reduction surgery without surgically removing a portion of the lung or sealing off a portion of the lung.

Applicants have found that a pneumostoma management system in accordance with embodiments of the present invention is desirable to maintain the patency of the pneumostoma and control flow of materials between the exterior of the patient and the parenchymal tissue of the lung via a pneumostoma. The pneumostoma management system includes a two-component pneumostoma management device and may also include one or more of the associated tools, packaging and methods described herein.

Pneumostoma Management Device

Figure 2A:
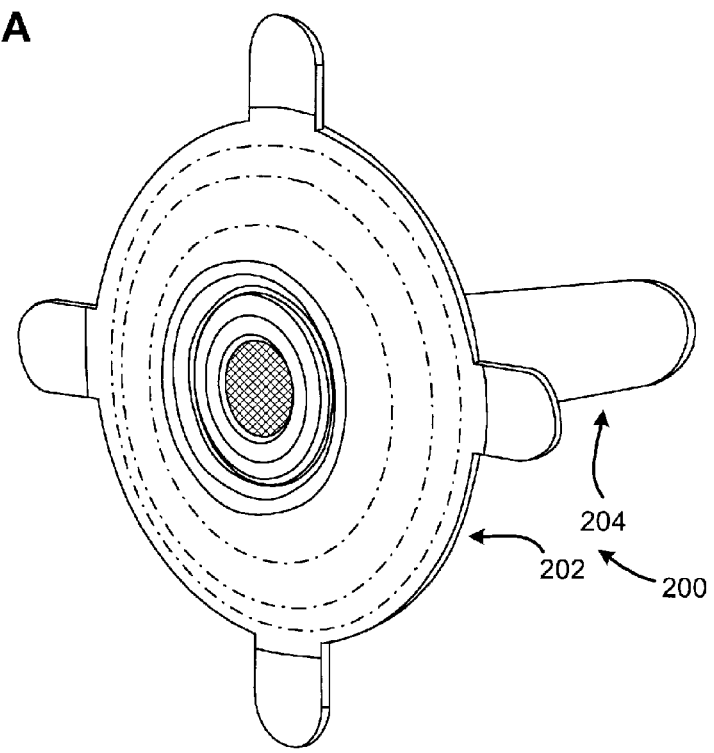
FIG. 2A shows a perspective view of components of a pneumostoma management system according to an embodiment of the present invention.
Figure 2B:
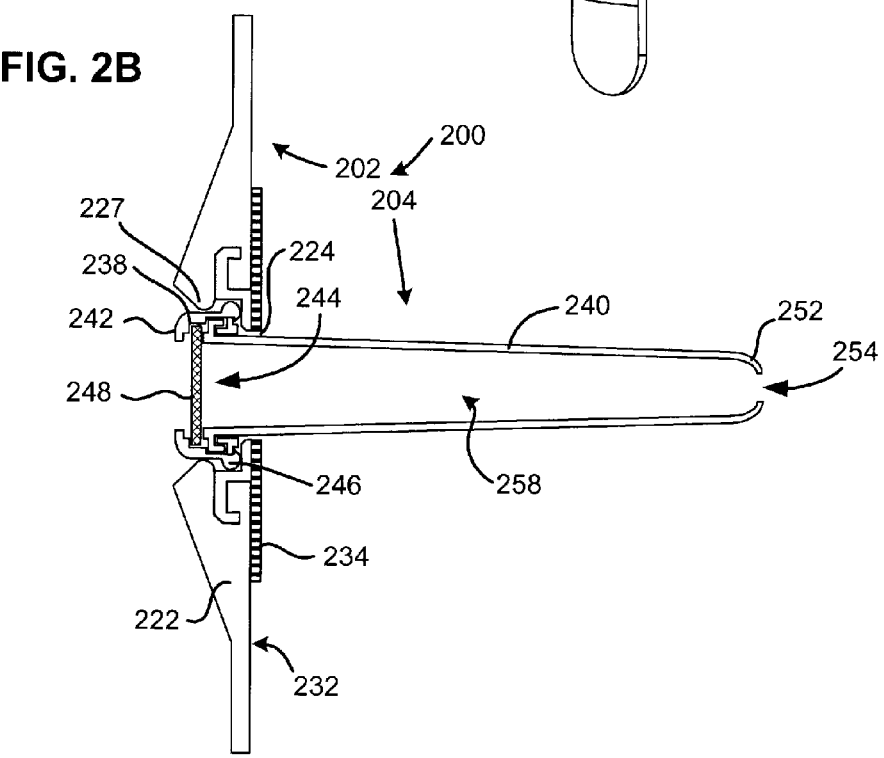
FIG. 2B shows a sectional view of the components of FIG. 2A.

FIGS. 2A and 2B illustrate views of a pneumostoma management device ("PMD") 200 in accordance with an embodiment of the present invention. PMD 200 includes a chest mount 202 which may be mounted to the skin of the patient and a pneumostoma vent 204 which is fitted to the chest mount 202. In a preferred embodiment pneumostoma vent 204 is mounted though an aperture 224 in chest mount 202. Chest mount 202 has a first coupling that engages a second coupling of the pneumostoma vent to releasably secure the pneumostoma vent 204 to the chest mount 202. As will be further described below, the joining between the two components is engineered so as to ensure that pneumostoma vent 204 cannot be over-inserted into the lung if it separates from chest mount 202. In preferred embodiments, pneumostoma vent 204 is formed from biocompatible/implantable polymers or biocompatible/implantable metals. In preferred embodiments, chest mount 202 is also formed from biocompatible polymers or biocompatible metals. A patient will typically wear a PMD at all times, and, thus, the materials should meet high standards for biocompatibility. A further description of suitable materials for manufacturing a PMD are provided in the Materials section below.

Pneumostoma vent 204 includes a tube 240 sized and configured to fit within the channel of a pneumostoma. Tube 240 is stiff enough that it may be inserted into a pneumostoma without collapsing. Over time a pneumostoma may constrict and it is one function of PMD 200 to preserve the patency of the channel of the pneumostoma by resisting the natural tendency of the pneumostoma to constrict. A crush recoverable material may be incorporated into tube 240 in order to make it crush recoverable. In one example, Nitinol, or another superelastic material, incorporated into tube 240 will give the tube collapse resistance and collapse recovery properties.

Tube 240 of pneumostoma vent 204 is sufficiently long that it can pass through the thoracic wall and into the cavity of a pneumostoma inside the lung. Pneumostoma vent 204 is not, however, so long that it penetrates so far into the lung that it might interfere with a major blood vessel. Fortunately, the larger blood vessels of the lung are located centrally and associated with the bronchi. Thus, the pneumostoma will typically only be adjacent to smaller peripheral blood vessels and risk from injury by the pneumostoma vent is small.

The length of tube 240 required for a pneumostoma vent 204 varies significantly between different pneumostomas. A longer tube 240 is usually required in patients with larger amounts of body fat on the chest. A longer tube 240 is usually required where the pneumostoma is placed in the lateral position 112 rather than the frontal position 110. Because of the variation in pneumostomas, pneumostoma vents 204 are manufactured having tubes 240 in a range of sizes and a patient is provided with a pneumostoma vent 204 having a tube 240 of appropriate length for the patient's pneumostoma. Tube 240 may be from 30 to 120 mm in length and from 5 mm to 20 mm in diameter depending on the size of a pneumostoma. A typical tube 240 may be between 40 mm and 80 mm in length and between 8 mm and 12 mm in diameter. In alternative embodiments a pneumostoma vent 204 is made with a single length (such as 120 mm) of tube 240 and tube 240 is then cut to the length appropriate for a particular patient.

Tube 240 of pneumostoma vent 204 preferably comprises an atraumatic tip 252 at the distal end as shown in FIGS. 2A and 2B. (This application uses the terms proximal and distal regarding the components of the pneumostoma management system in the conventional manner. Thus, proximal refers to the end or side of a device closest to the hand operating the device, whereas distal refers to the end or side of a device furthest from the hand operating the device.) Tip 252 may be rounded, beveled or curved in order to reduce irritation or damage to the tissues of the pneumostoma or lung during insertion or while in position. Where a single length tube 240 is provided and subsequently cut to length it is desirable that the tube be shaped such that at each of a plurality of cut points cutting will generate an atraumatic tip. This can be achieved, for example, by including a series of rounded narrow points on tube 240.

The material and thickness of tube 240 of pneumostoma vent 204 is selected such that tube 240 is soft enough that it will deform rather than cause injury to the pneumostoma or lung. Pneumostoma vent 204 has an opening 254 in tip 252 of tube 240. Opening 254 allows the entry of gases from the cavity of the pneumostoma into lumen 258 of tube 240. Tube 240 is optionally provided with one or more side openings (not shown) positioned near tip 252 and/or along the length of tube 240 to facilitate the flow of gas and/or mucous/discharge into lumen 258.

Pneumostoma vent 204 includes a cap 242 and a hydrophobic filter 248 over the opening 244 in the proximal end of tube 240. Hydrophobic filter 248 is positioned over the proximal opening 244 into lumen 258. Hydrophobic filter 248 is positioned and mounted such that material moving between lumen 258 and the exterior of pneumostoma vent 204 must pass through hydrophobic filter 248. Hydrophobic filter 248 is preferably designed such that it may be fit into a recess in cap 242. As shown in FIG. 2B, cap 242 comprises a recess 238 into which hydrophobic filter 248 may be fit. Hydrophobic filter 248 may, alternatively, be fitted into cap 242 using a joint such as a threaded coupling or adhesive or, in some cases, formed integrally with cap 242. Hydrophobic filter 248 may be made from a material such as medical grade GORE-TEX® material (W. L. Gore & Associates, Inc., Flagstaff, Ariz.). As shown in FIG. 2F, a snap ring 243 locks cap 242 and hydrophobic filter 248 onto the proximal end of tube 240.

Hydrophobic filter 248 serves several purposes. In general, hydrophobic filter 248 controls the passage of solid or liquid material between the lumen 258 and the exterior of cap 242. For example, hydrophobic filter 248 prevents the flow of water into the lumen 258 through proximal opening 244. Thus, a patient using PMD 200 may shower without water entering the lung through the pneumostoma. Hydrophobic filter 248 may also be selected so as to prevent the entry of microbes, pollen and other allergens and pathogens into the lumen 258. Hydrophobic filter 248 also prevents the exit of liquid and particulate discharge from lumen 258 to the exterior of pneumostoma vent 204. This is desirable to prevent contact between liquid and particulate discharge and clothing, for example.

Chest mount 202 connects to the proximal end of pneumostoma vent 204. In one embodiment, illustrated in FIGS. 2A and 2B, chest mount 202 comprises a flange 222 and an aperture 224. The aperture 224 is adapted and configured to receive the pneumostoma vent 204. Chest mount 202 is designed to have a smooth surface and a low profile so it is comfortable for the patient to wear. Chest mount 202 should be designed so as not to snag on the patient's clothing or to restrict motion of the patient's arm (if placed in a lateral pneumostoma 112). Flange 222 is significantly wider than pneumostoma vent 204. Flange 222, thus, comprises a contact surface 232 which contacts the skin of the patient surrounding the pneumostoma and positions the aperture 224 over the opening of the pneumostoma. Flange 222 is designed such that it is sufficiently flexible that it can conform to the surface of the chest. Contact surface 232 is also provided with a pad of biocompatible adhesive 234, such as a hydrocolloid adhesive, for securing flange 222 to the skin of the patient. The adhesive 234 may be protected by a protector sheet that is removed prior to use of flange 222. Adhesive 234 should be selected so as to secure flange 222 to the chest of the patient in the correct position relative to the pneumostoma without causing undue irritation to the skin of the patient. The adhesive need not create an air tight seal between flange 222 and the skin of the patient. Suitable adhesive pads are available commercially from Avery Dennison (Painesville, Ohio).

Referring now to FIG. 2C, which shows a perspective view of chest mount 202 without pneumostoma vent 204. Flange 222 is generally circular but is provided with one or more tabs 236 to facilitate application and removal of flange 222 from the skin of the patient. As shown in FIG. 2C, chest mount 202 comprises an aperture 224 through which tube 240 of pneumostoma vent 204 may be inserted. Flange 222 is slightly convex on the upper surface 235. Flange 222 includes a recess 226 into which cap 242 of pneumostoma vent 204 may be press fit. Flange 222 is thick enough in the region of aperture 224 to receive the cap 242 of pneumostoma vent 204 so that the cap of pneumostoma vent 204 is flush with the upper surface 235 of flange 222. Recess 226 forms a coupling adapted to releasably secure the cap 242 of pneumostoma vent 204 into flange 222. As shown in FIGS. 2B and 2C, recess 226 has a lip 227 to releasably secure the cap 242 of pneumostoma vent 204 into flange 222. However, other couplings may be used to releasably secure pneumostoma vent 204 to chest mount 202 including clips, pins, snaps, catches, threaded joints, temporary adhesive and the like.

In a preferred embodiment, an aperture plate 228 is embedded in the conformable polymer of flange 222. FIG. 2D shows a perspective view of an aperture plate 228 that is embedded within flange 222 of chest mount 202. Note that aperture plate 228 surrounds aperture 224 of chest mount 202. Aperture plate 228 is made of a stiffer, less compliant material than flange 222 in order that the dimensions of aperture 224 are tightly controlled. Because aperture plate 228 is stiff enough that the size and shape of aperture 224 remains stable even under any reasonably possible application of force to chest mount 202.

Referring now to FIG. 2E which shows a perspective view of pneumostoma vent 204 without chest mount 202. Cap 242 is attached to the proximal end of tube 240. Hydrophobic filter 248 is sandwiched between cap 242 and tube 240. An opening 244 in cap 242 communicates with the lumen 258 of tube 240 via hydrophobic filter 248. As shown in FIGS. 2B and 2E, cap 242 comprises a lip 246 which releasably engages lip 227 of recess 226 of flange 222 to secure pneumostoma vent 204 within the recess 226 of flange 222. Lip 246 forms a coupling element of pneumostoma vent 204 that cooperates with recess 226 to releasably secure pneumostoma vent 204 into chest mount 202 with tube 240 positioned through aperture 224.

FIG. 2F shows an exploded view of pneumostoma vent 204 showing the individual components of pneumostoma vent 204. Hydrophobic filter 248 is sandwiched between tube 240 and cap 242. Tube 240 has a flange 241 at its proximal end. Snap ring 243 slides over tube 240. The inner diameter of snap ring 243 is too small to pass over flange 241, and, thus, when snap ring 243 is locked into cap 242, tube 240 is locked to cap 242. It should be noted that the outer diameter of each of snap ring 243, hydrophobic filter 248, flange 241 and cap 242 is larger than the diameter of aperture 224 of aperture plate 228. Aperture plate 228 is sufficiently stiff that the dimensions of aperture 224 will not change even under loads significantly higher than would be expected during use of the device. Thus, snap ring 243, hydrophobic filter 248, flange 241 and cap 242 cannot pass through aperture 224 into the pneumostoma. Distal tip 252 of tube 240 and the body of tube 240 are small enough to pass through aperture 224 however, flange 241 and/or cap 242 serve to limit the passage of tube 240 through aperture 224. These safety features prevent unsafe entry of any of the components of pneumostoma vent 204 into the pneumostoma even in the unlikely event of device failure. Likewise all the components of the chest mount 202 such as flange 222 and aperture plate 224 are significantly larger than the aperture of a pneumostoma thus precluding passage of any component of the chest mount 202 into a pneumostoma even in the unlikely event of device failure.

Insertion Tool

The pneumostoma management system may also include insertion and/or removal tools for use with pneumostoma vent 204. The tools help control insertion and removal of pneumostoma vent 204 and also help maintain sterility of pneumostoma vent 204 before and during insertion into a pneumostoma. FIGS. 3A-3F show views of an insertion tool 300 which forms part of the pneumostoma system according to one embodiment of the invention.

Figure 3A:
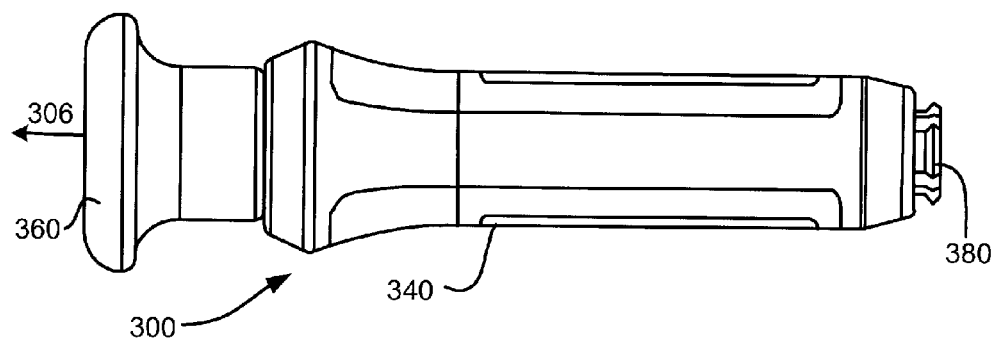
FIG. 3A shows an insertion tool of a pneumostoma management system according to an embodiment of the present invention.

Referring now to FIG. 3A which shows an external view of insertion tool 300. Insertion tool 300 includes a casing 340, having a handle 360 at the proximal end and a grasper 380 at the distal end. The tool also comprises an end cap 320 at the distal end of casing 340 (not shown in FIG. 3A). When handle 360 is pushed up against the distal end of casing 340, grasper 380 is configured to lock to the cap of a pneumostoma vent. When handle 360 is pulled away from casing 340 in the direction of arrow 306, grasper 380 is configured to release the cap of a pneumostoma vent. Insertion tool 300 includes an internal mechanism that allows handle 360 to be moved away from casing 340 in the direction of arrow 306 one time and then locks handle 360 in place. Thus, handle 360 is a single use device. Handle 360 is provided in sterile packaging, the one-time-use lock protects the no-longer-sterile insertion tool from reuse.

Figure 3B:
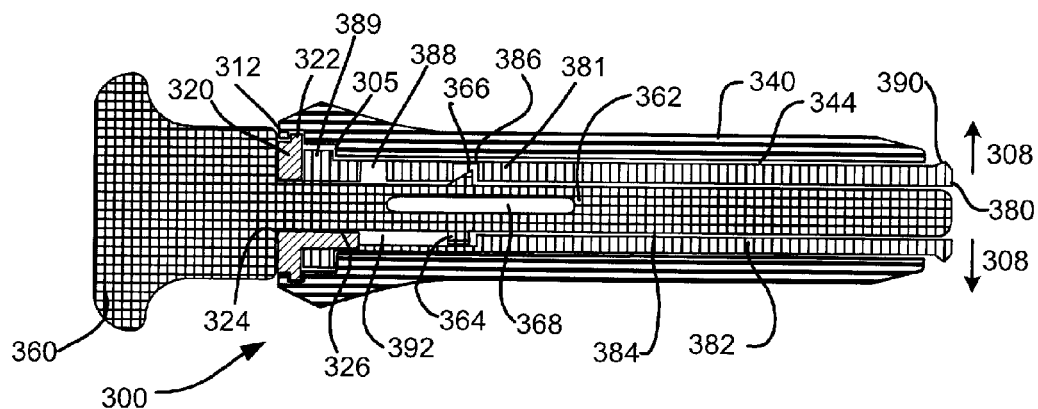
FIGS. 3B-3F show aspects of the components and operation of the insertion tool of FIG. 3A.

FIG. 3B shows a sectional view of insertion tool 300. Casing 340 has a central lumen 344 running from the proximal end to the distal end. End cap 320 is designed such that it may be snap fit into the proximal end of casing 340 to lock together the components of insertion tool 300 without the use of adhesive. End Cap 320 has a step 322 which is engaged by lip 312 of casing 340. End cap 320 has an opening 324 through which a portion of the handle 360 is received. End cap 320 also has a tongue 326 that protrudes into casing 340.

Handle 360 includes a mandrel 362. In this embodiment the handle and mandrel are formed in one piece. Mandrel 362 comprises a square tab 364 and a ramped tab 366. Tabs 364 and 366 are on opposite sides of slot 368 in mandrel 362. Slot 368 is sized and configured such that mandrel 362 is sufficiently flexible in the region of tabs 364 and 366 for the tabs to be pushed towards each other slightly by compressing slot 368. The portion of handle 360 external to casing 340 is too large to enter casing 340 thus precluding over insertion.

Grasper 380 comprises four arms 382 attached to a tubular section 381 (only two arms shown in sectional view). Between the arms 382 is a space 384 for receiving mandrel 362. The space narrows slightly towards the distal end of the arms 382 because arms 382 ramp up slightly in thickness towards the distal end. On the distal end of each of arm 382 is a wedge 390. In the tubular section 381 of grasper 380 there is a proximal detent 386 and a distal detent 388 for receiving ramped tab 366 of mandrel 362. In the tubular section 381 of grasper 380 there is also a slot 392 opposite detents 386 and 388 for receiving square tab 366 of mandrel 362. The proximal end of tubular section 381 has a lip 389 which engages a recess 305 of the casing 340 to fix the location of grasper 380 and preclude passage of grasper 380 through casing 340.

To assemble insertion tool 300, mandrel 362 is inserted through opening 324 in end cap 320. Tabs 364, 366 are pushed towards one another compressing slot 368 as the tabs pass through opening 324 which would otherwise be too narrow to allow tabs 364, 366 to pass. Mandrel 362 is then inserted through the tubular section 381 of grasper 380 and between arms 382 until ramped tab 366 is located in distal detent 388 and square tab 364 is located in slot 392. Casing 340 is then pushed over grasper 380 until step 322 of end cap 320 engages lip 312 at the proximal end of casing 340. Note that for ease of manufacturing insertion tool comprises only four components casing 340, grasper 380, handle 360 and end cap 320. Moreover, to ensure all failure modes are as safe as possible, each of the grasper 380, handle 360 and end cap 320 is too large to pass through casing 340 any further than is necessary for their function.

Figure 3C:
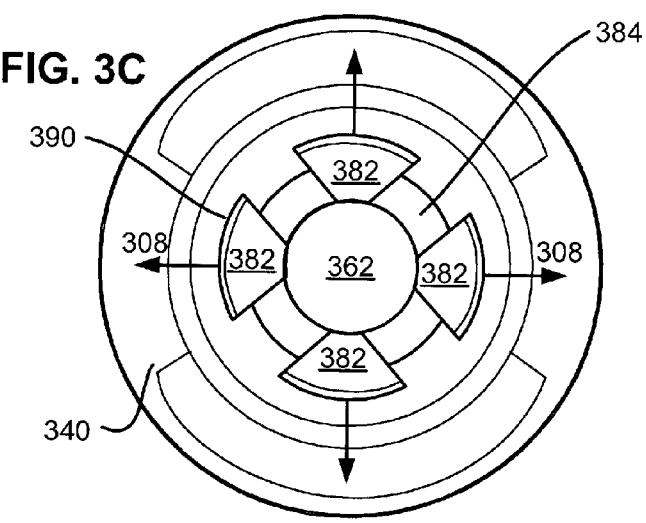

Insertion tool 300 is assembled in its locked configuration as shown in FIGS. 3B and 3C. In this locked configuration of the insertion tool, as shown in FIG. 3B, mandrel 362 fills the space between 384 between arms 382 locking wedges 390 outward as shown by arrows 308. Ramped tab 366 of mandrel 362 is in distal detent 386 of tubular section 381. FIG. 3C shows a view of the distal end of insertion tool 300 in the locked configuration. Note that each of arms 382 has been forced to its outermost position by the presence of mandrel 362 at the distal end of its travel in space 384.

Figure 3D:
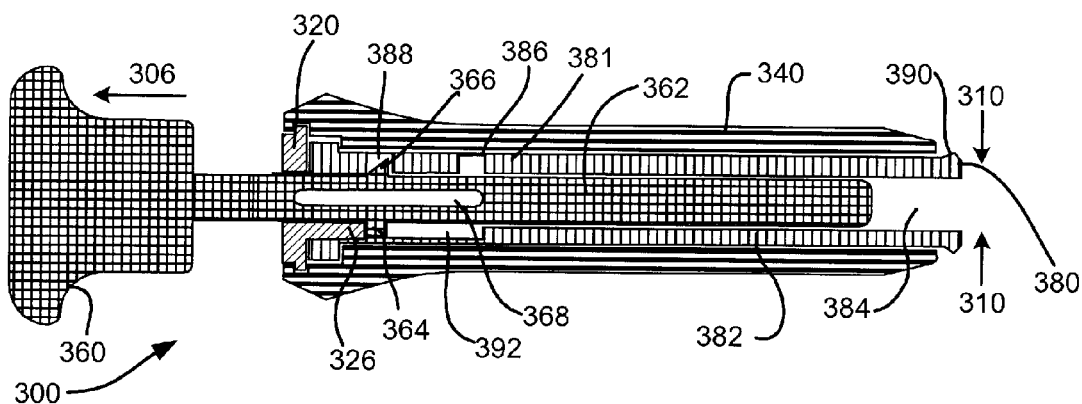

To release insertion tool 300, handle 360 is pulled in the direction shown by arrow 308 relative to casing 340. As shown in FIG. 3D, ramped tab 366 is oriented such that the motion of handle 360 in the direction 306 compresses slot 368 allowing ramped tab 366 to pass out of distal detent 386. Square tab 364 rides in slot 392 so that mandrel 362 does not rotate relative to tubular section 381. When ramped tab 366 reaches proximal detent 388, the slot 368 is decompressed and ramped tab 366 is pushed into proximal detent 388. Note that ramped tab 366 is oriented such that it is caught in proximal detent 388 and cannot be returned from proximal detent 388 to distal detent 386. The travel of square tab 364 is also limited by tongue 326 of end cap 320 so as to prevent removal of handle 360 from casing 340. Thus, handle 360 is now fixed in the unlocked configuration.

Figure 3E:
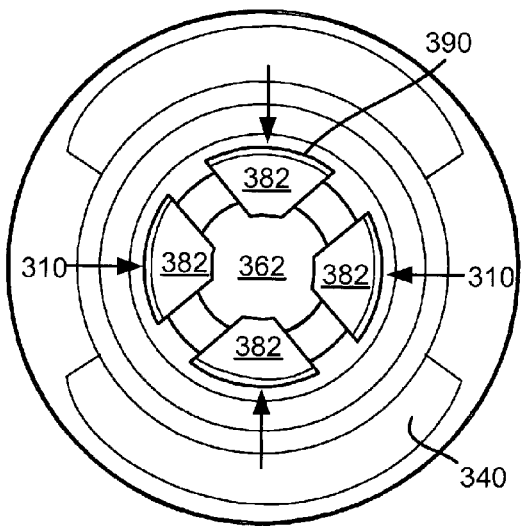
Figure 3F:
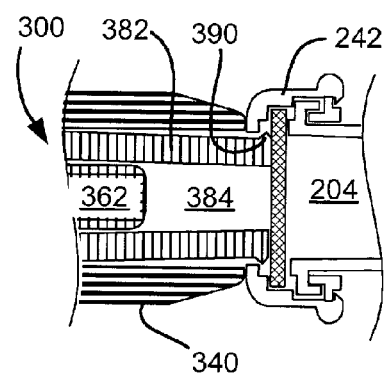

In this unlocked configuration, shown in FIGS. 3D, 3E and 3F, the distal end of mandrel 362 is retracted away from the distal end of casing 340. Consequently, space 384 is vacant between arms 382 of grasper 380. As a consequence, wedges 390 may move inward as shown by arrows 310 because of the flexibility of arms 382 no longer constrained by the presence of mandrel 362. FIG. 3E shows a view of the distal end of insertion tool 300 in the unlocked configuration note that each of arms 382 has moved to an inner position because mandrel 362 has been withdrawn from the distal end of space 384. FIG. 3F shows a close-up of the distal end of insertion tool 300 showing how inward displacement of arms 382, because of retraction of mandrel 362, allows wedges 390 to disengage a cap 242 of a pneumostoma vent 204. Thus, in this unlocked configuration of the insertion tool 300, insertion tool 300 releases pneumostoma vent 204 after insertion into a pneumostoma.

Removal Tool

The pneumostoma management system may also include insertion and/or removal tools for use with pneumostoma vent 204. The tools help control insertion and removal of pneumostoma vent 204 and also help maintain sterility of pneumostoma vent 204 before and during insertion into a pneumostoma. FIGS. 4A-4F show views of an insertion tool 400 which forms part of the pneumostoma system according to one embodiment of the invention.

Figure 4A:
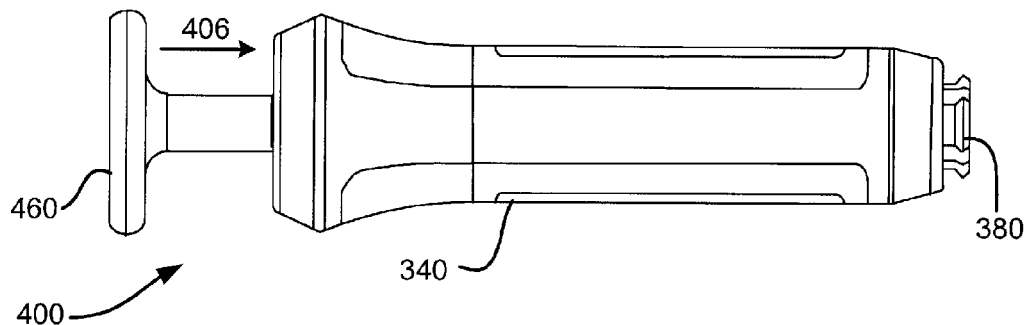
FIG. 4A shows a removal tool of a pneumostoma management system according to an embodiment of the present invention.

Referring now to FIG. 4A which shows an external view of removal tool 400. Removal tool 400, in this embodiment, comprises the same casing 340, grasper 380 and end cap 320 as insertion tool 300. The structural difference between removal tool 400 and insertion tool 300 is handle 460. The starting position for handle 460 is, as shown in FIG. 4A, spaced away from casing 340. In this unlocked configuration grasper 380 may be inserted into the cap of a pneumostoma vent. However, when handle 460 is pushed against casing 340, as shown by arrow 406, removal tool 400 changes to the locked configuration and is secured to the cap of a pneumostoma vent allowing the pneumostoma vent to be removed from a chest mount. Removal tool 400 includes an internal mechanism that only allows handle 460 to be moved towards casing 340 in the direction of arrow 406 one time and then locks handle 460 in place. Thus, removal tool 400 is a single use device. When removal tool 400 is secured to a pneumostoma vent for removal, the removal tool and pneumostoma vent are locked to one another and are disposed of in that from. The one-time-use lock protects the no-longer-sterile removal tool and pneumostoma vent from reuse.

Figure 4B:
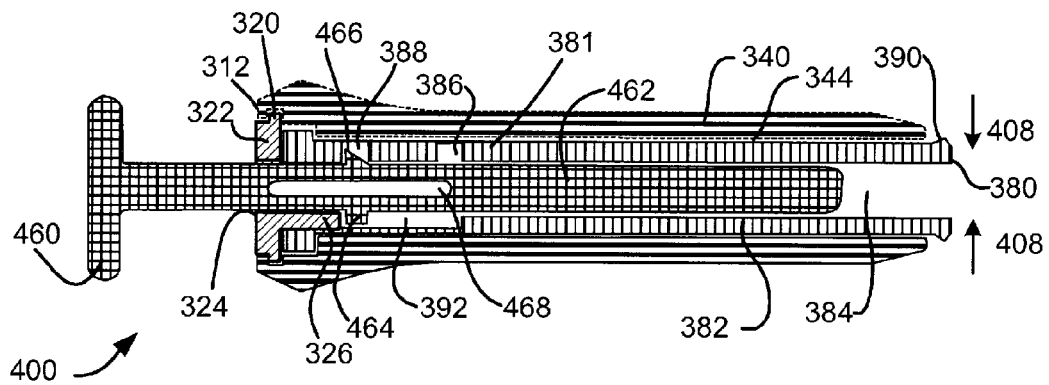
FIGS. 4B-4F show aspects of the components and operation of the removal tool of FIG. 4A.

FIG. 4B shows a sectional view of removal tool 400. The internal components of removal tool 400 are the same as for insertion tool 300 with the exception of handle 460 and mandrel 462. Handle 460 and mandrel 462 are formed in one piece. Note that mandrel 462 comprises a square tab 464 and a ramped tab 466. Tabs 464 and 466 are on opposite sides of slot 468 in mandrel 462. Slot 468 is sized and configured such that mandrel 462 is sufficiently flexible in the region of tabs 464 and 466 for the tabs to be pushed towards each other slightly by compressing slot 468. However, in mandrel 462, ramped tab 466 is ramped in the opposite direction to ramped tab 366 of the insertion tool. Moreover, ramped tab 466, square tab 464 and slot 468 are located such that in the unlocked configuration, ramped tab 466 occupies proximal detent 388 of grasper 380 and square tab 464 is at the proximal end of slot 392. Note that for ease of manufacturing, removal tool 400 and insertion tool 300 share three out of four components. Thus, only five different components (casing 340, grasper 380, handle 360, handle 460 and end cap 320) are required to make both the insertion tool 300 and removal tool 400. Moreover, to ensure all failure modes are as safe as possible, each of the grasper 380, handle 360, handle 460 and end cap 320 is too large to pass through casing 340 any further than is necessary for their function.

Removal tool 400 is assembled in the same way as insertion tool 300; mandrel 462 is first inserted through opening 324 in end cap 320. Tabs 464, 466 are pushed towards one another, compressing slot 468 as the tabs pass through opening 324, which would otherwise be too narrow to allow tabs 464, 466 to pass. Mandrel 462 is then inserted through the tubular section 381 of grasper 380 and between arms 382 until ramped tab 466 is located in proximal detent 388 and square tab 464 is located in slot 392. Casing 340 is then pushed over grasper 380 until step 322 of end cap 320 engages lip 312 at the proximal end of casing 340.

Figure 4C:
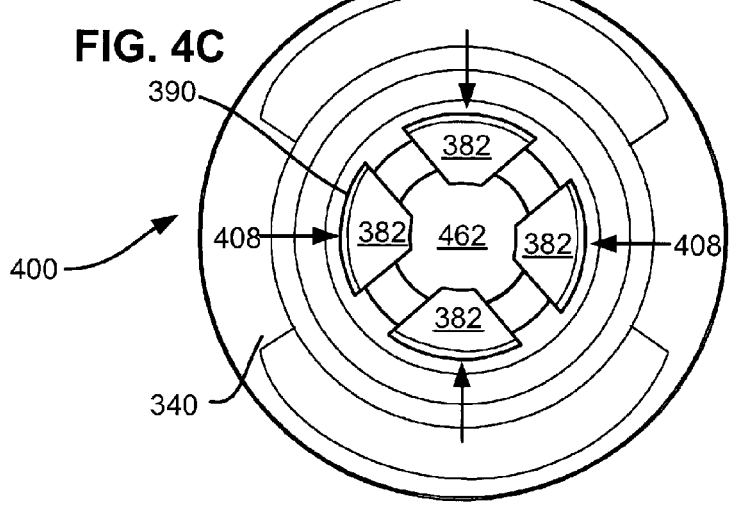

Removal tool 400 is assembled in its unlocked configuration as shown in FIGS. 4B and 4C. In this unlocked configuration of the removal tool 400, mandrel 462 does not fill the space 384 between arms 382. Thus, wedges 390 can move inward as shown by arrows 408. Ramped tab 466 of mandrel 462 is in proximal detent 388 of tubular section 381. FIG. 4C shows view of the distal end of removal tool 400 in the unlocked configuration. Note that each of arms 382 can travel inwards because mandrel 462 is not at the distal end of its travel in space 384.

Figure 4D:
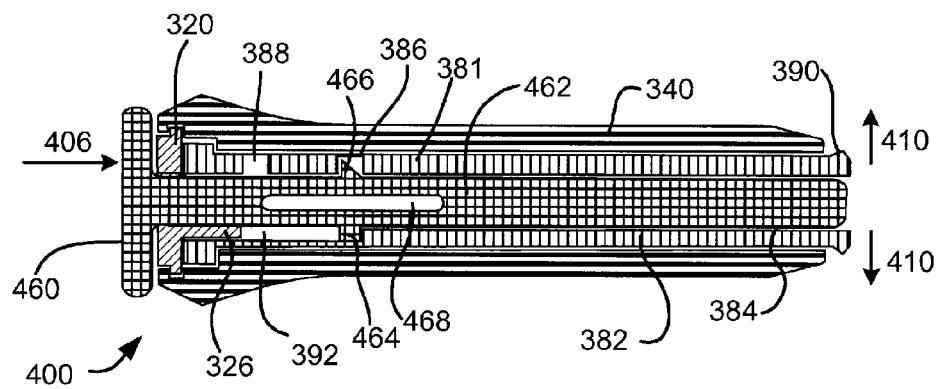

To secure removal tool 400 to a pneumostoma tube, handle 460 is pushed in the direction shown by arrow 406 relative to casing 340. As shown in FIG. 4D, ramped tab 466 is oriented such that the motion of handle 460 compresses slot 468 allowing ramped tab 466 to pass out of proximal detent 388. Square tab 464 rides in slot 392 so that mandrel 462 does not rotate relative to tubular section 381. When ramped tab 466 reaches distal detent 386, the slot 468 is decompressed and ramped tab 466 is pushed into distal detent 386. Note that ramped tab 466 is oriented such that it is caught in distal detent 386 and cannot be returned from distal detent 386 to proximal detent 388. Thus, handle 460 is now fixed in the locked configuration. The travel of square tab 464 is also limited by tongue 326 of end cap 320 so as to prevent removal of handle 460 from casing 340.

Figure 4E:
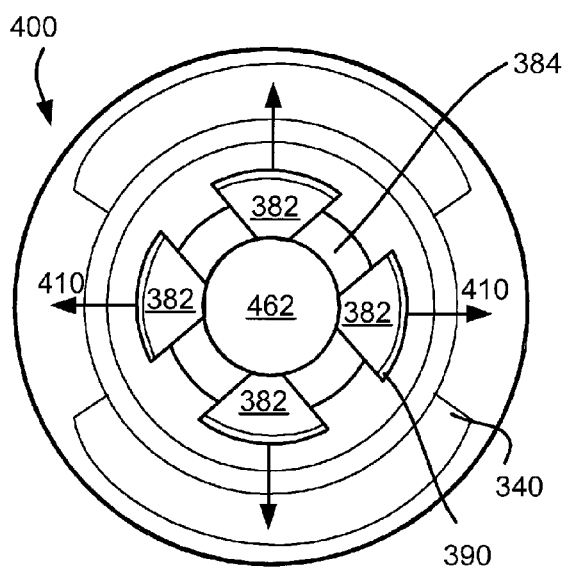
Figure 4F:
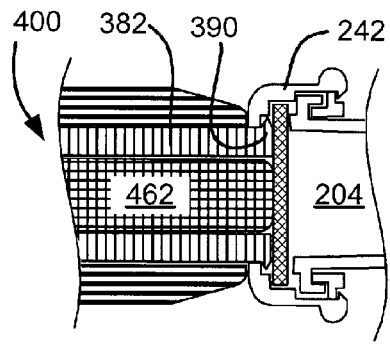

In the locked configuration of the removal tool shown in FIGS. 4D-F, the distal end of mandrel 462 is pushed into the distal end of casing 340. Consequently mandrel 462 fills space 384 and pushes arms 382 outward as shown by arrows 410. FIG. 4E shows view of the distal end of removal tool 400 in the locked configuration. Note that each of arms 382 has moved to its outer position because mandrel 462 has been pushed to the distal end of space 384. FIG. 4F shows a close-up of the distal end of removal tool 400 showing how outward displacement of arms 382 by mandrel 462 causes wedges 390 to engage cap 242 of a pneumostoma vent 204. Thus, in this locked configuration of removal tool 400, removal tool 400 is secured to pneumostoma vent 204 allowing it to be removed from the pneumostoma.

Materials

In preferred embodiments, pneumostoma vent 204 and chest mount 202 of PMD 200 are formed from biocompatible polymers or biocompatible metals. A patient will typically wear PMD 200 at all times, and, thus, the materials, particularly of tube 240, should meet high standards for biocompatibility. In general, preferred materials for manufacturing PMD 200 are biocompatible thermoplastic elastomers that are readily utilized in injection molding and extrusion processing. As will be appreciated, other suitable similarly biocompatible thermoplastic or thermoplastic polymer materials can be used without departing from the scope of the invention. Biocompatible polymers for manufacturing PMD may be selected from the group consisting of polyethylenes (HDPE), polyvinyl chloride, polyacrylates (polyethyl acrylate and polymethyl acrylate, polymethyl methacrylate, polymethylcoethyl acrylate, ethylene/ethyl acrylate), polycarbonate urethane (BIONATE®), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyarylether-etherketone, polyetheretherketone, polyetherether-ketoneketone, polyetherketoneether-ketoneketone polyetherketone), polyether block amides (PEBAX®), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers in general. Reference to appropriate polymers that can be used for manufacturing PMD 200 can be found in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the PMD include medical grade inorganic materials such stainless steel, titanium, ceramics and coated materials.

Additionally, the tube 240 of pneumostoma vent 204 may be designed to deliver a pharmaceutically-active substance. For purposes of the present disclosure, an "active pharmaceutical substance" is an active ingredient of vegetable, animal or synthetic origin which is used in a suitable dosage as a therapeutic agent for influencing conditions or functions of the body, as a replacement for active ingredients naturally produced by the human or animal body and to eliminate or neutralize disease pathogens or exogenous substances. The release of the substance in the environment of pneumostoma vent 204 has an effect on the course of healing and/or counteracts pathological changes in the tissue due to the presence of pneumostoma vent 204. In particular, it is desirable in some embodiments to coat or impregnate pneumostoma vent 204 with pharmaceutically-active substances that preserve the patency of pneumostoma and/or are antimicrobial in nature but that do not unduly irritate the tissues of the pneumostoma.

In particular cases, suitable pharmaceutically-active substances may have an anti-inflammatory and/or antiproliferative and/or spasmolytic and/or endothelium-forming effect, so that the functionality of the pneumostoma is maintained. Suitable pharmaceutically-active substances include: anti-proliferative/antimitotic agents including natural products such as vinca alkaloids (i.e. vinblastine, vincristine, and vinorelbine), paclitaxel, epipidophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) llb/llla inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (inaperturethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof, cell cycle inhibitors, mTOR inhibitors, and growth factor receptor signal transduction kinase inhibitors; retenoids; cyclin/CDK inhibitors; HMG co-enzyme reductase inhibitors (statins); silver compound and protease inhibitors.

In some embodiments, the active pharmaceutical substance to be coated upon or impregnated in the pneumostoma vent 204 is selected from the group consisting of amino acids, anabolics, analgesics and antagonists, anaesthetics, anti-adrenergic agents, anti-asthmatics, anti-atherosclerotics, antibacterials, anticholesterolics, anti-coagulants, antidepressants, antidotes, anti-emetics, anti-epileptic drugs, antifibrinolytics, anti-inflammatory agents, antihypertensives, antimetabolites, antimigraine agents, antimycotics, antinauseants, antineoplastics, anti-obesity agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and neurotrophins, osmotic diuretics, parasympatholytics, para-sympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, saccharides, polysaccharides, glycoproteins, hyaluronic acid, and any excipient that can be used to stabilize a proteinaceous therapeutic.

Hydrophobic filter 248 should be sufficiently porous to allow air to exit through the filter. Materials for hydrophobic filters are available commercially and filters can be fabricated from any suitable hydrophobic polymer, such as tetrafluoroethylene, PTFE, polyolefins, microglass, polyethylene and polypropylene or a mixture thereof. In preferred examples, the hydrophobic filter is a laminated tetrafluoroethylene e.g. TEFLON®, (E.I. du Pont de Nemours Co.) or GORE-TEX® (W.L. Gore, Inc.) of a controlled pore size. In other examples the hydrophobic filter may comprise a felted polypropylene; PTFE/polypropylene filter media. Hydrophobic filter 248 may additionally comprise an antimicrobial, an anti-bacterial, and/or an anti-viral material or agent.

Insertion tool 300 and removal tool 400 do not contact the pneumostoma. Thus, the materials of insertion tool 300 and removal tool 400 do not have to be biocompatible and implantable materials. Suitable materials for making insertion tool 300 and removal tool 400 include medical grade metals, plastics, acrylics and resins. In a preferred embodiment, the insertion tool, removal tool and alignment tools may be made from ABS (Acrylonitrile-Butadiene-Styrene) plastic. In a preferred embodiment, the insertion and removal tool are made of the same material as aperture plate 228 and cap 242.

Use of The Pneumostoma Management System

The pneumostoma management system is designed such that the system may be used by a patient in a sterile manner. After creating and healing of the pneumostoma the patient will be responsible for applying and removing the chest mount 202 and the insertion, removal and disposal of pneumostoma vent 204. The patient will exchange one pneumostoma vent 204 for another and dispose of the used pneumostoma vent 204. Pneumostoma vent 204 will be replaced periodically, such as daily, or when necessary. The patient will be provided with a supply of pneumostoma vent 204 by a medical practitioner or by prescription. Chest mount 202 will also be replaced periodically, such as weekly, or when necessary. The patient will also be provided with a supply of chest mount 202 by a medical practitioner or by prescription. A one week supply of pneumostoma vent 204 (such as seven pneumostoma vents 204) may be conveniently packaged together with one chest mount 202.

Figure 5A:
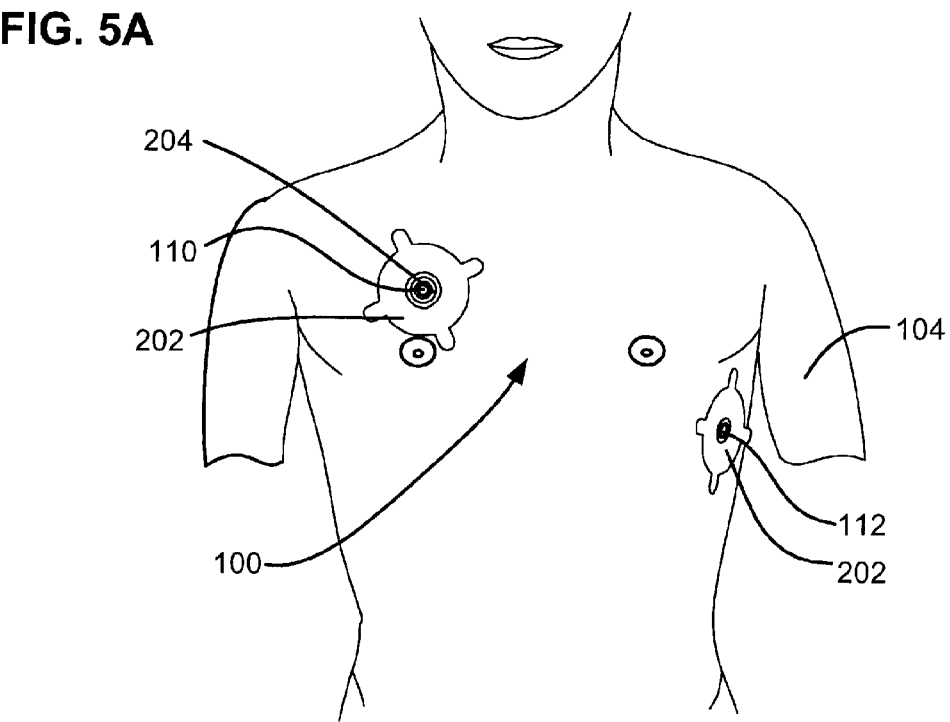
FIGS. 5A-5D show steps and tools for applying a chest mount according to embodiments of the present invention.

To use PMD 200, chest mount 202 is first positioned over a pneumostoma and secured with adhesive to the skin of the patient. In a preferred embodiment, the chest mount remains attached for up to a week thereby avoiding irritation of the skin caused by daily attachment and removal of a mount. FIG. 5A illustrates the positioning of chest mount 202 over pneumostoma 110 and pneumostoma 112 of FIG. 1A. As shown in FIG. 5A the low profile of chest mount 202 allows it to be inconspicuously positioned on the chest 100 of a patient in either the frontal 110 (over the right lung) or lateral 112 (over the fourth or fifth intercostal space under the left arm 104) locations. PMD 200 is designed so as not to interfere with the range of motion or clothing of the patient. This is of importance for a device such as PMD 200 which must be used continuously to be effective. Comfort and ease of use are important if patient compliance with treatment protocols is to be achieved. Chest mount 202 may be positioned by the patient by manual alignment of the aperture 204 of chest mount 202 with the aperture of the pneumostoma. Alternatively, a pneumostoma vent or an alignment tool may be used to align the chest mount.

In one embodiment, the chest mount 202 may be aligned with the pneumostoma 110 using a pneumostoma vent 204 and optionally an insertion tool 300. The chest mount 202 may be provided to the patient with the pneumostoma vent 204 and optional insertion tool as one assembly. Alternatively, the patient may insert the pneumostoma vent 204 into the chest mount 202 prior to applying chest mount 202 to the chest. The patient then manipulates the chest mount 202 by the tabs 236 or insertion tool 300. The patient places the tip of pneumostoma vent 204 into the aperture 126 of the pneumostoma 110 and pushes the pneumostoma vent 204 gently and slowly into the pneumostoma 110. During insertion the patient lets the pneumostoma vent 204 align itself with the channel 120 of the pneumostoma 110 such that when the chest mount 202 contacts and adheres to the skin 114 of the chest 100, the aperture 224 of the chest mount 202 is perfectly aligned with the aperture 126 of the pneumostoma 110. If an insertion tool 300 was used, the patient then pulls gently on handle 360 to detach the alignment tool 300 from the pneumostoma vent 204, leaving the chest mount 202 and pneumostoma vent 204 in place on the chest 100 of the patient.

Figure 5B:
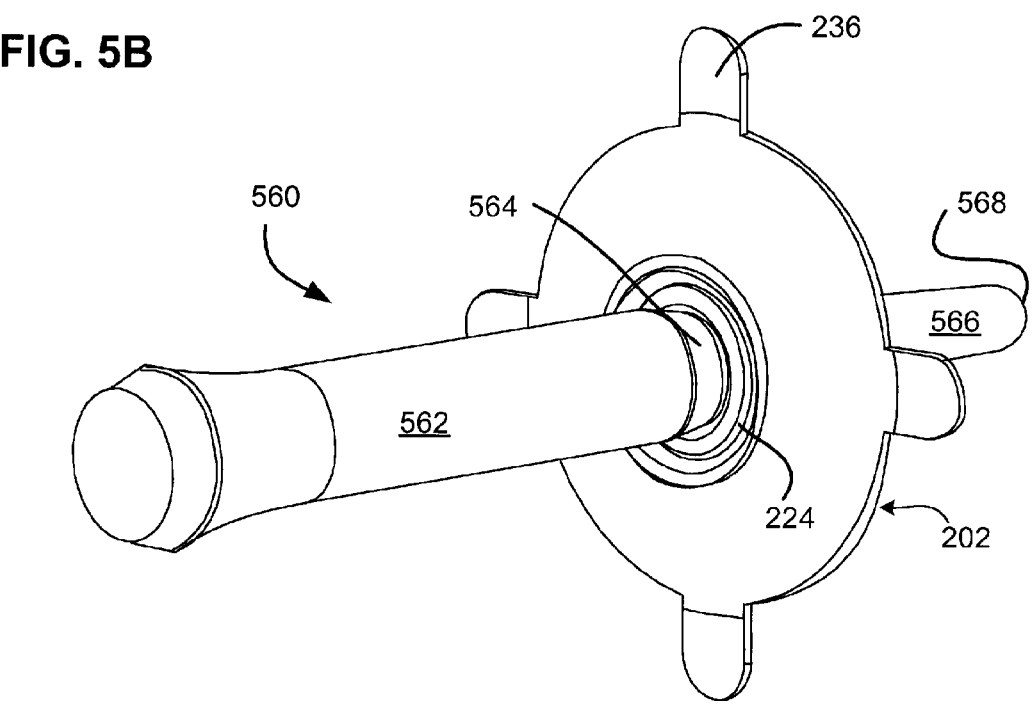
Figure 5C:
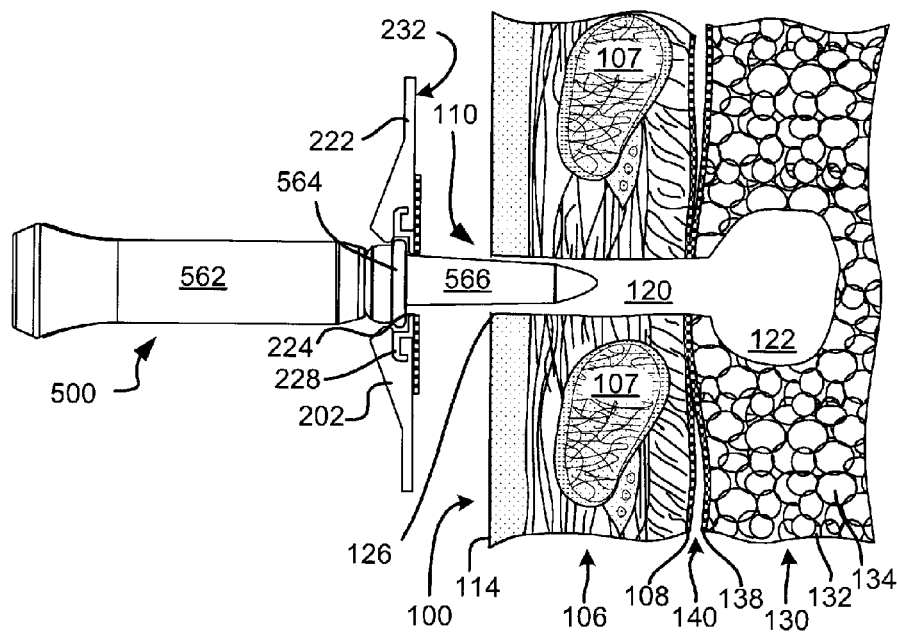

Alternatively, an alignment tool may be used during positioning of chest mount 202. FIGS. 5B and 5C show a chest mount alignment tool 560, 500, which aids positioning a chest mount 202 and aligning the aperture 224 of the chest mount 202 with an aperture of a pneumostoma. The alignment tool 560 comprises a handle section 562 joined to a mount engagement section 564 joined to a pneumostoma alignment probe 566. The handle is designed to be gripped by the patient while applying the chest mount 202. The handle 562 allows the chest mount 202 to be manipulated without direct handling of the chest mount 202 by the patient. This reduces the risk of contaminating the chest mount 202 and pneumostoma 110. Mount engagement section 564 is shaped similarly to the cap of a pneumostoma vent 204 and is designed to fit into and engage the recess 226 (shown in FIG. 2C) of a chest mount 202. Like the cap of a pneumostoma vent, the mount engagement section 564 is too large to pass through the aperture 224 of an aperture plate 228, and, thus, cannot be inserted too far through the chest mount 202. However, the pneumostoma alignment probe 566 fits through aperture 224 and protrudes a short distance beyond the contact surface 232 of the flange 222. Pneumostoma alignment probe 566 is preferably small enough that it will be suitable for use with all patients. Preferably, the length of pneumostoma alignment probe 566 is less than the length of the smallest available pneumostoma vent 204. Alignment tool 560 may be provided preassembled with a chest mount 202, as shown in FIG. 5B.

As shown in FIG. 5C, to apply the chest mount 202, the patient uses handle 562 to remove the chest mount 202 from its sterile packaging. The patient then removes any protective covering over the adhesive on the contact surface 232 of the chest mount 202. The patient then places the tip of pneumostoma alignment probe 566 into the aperture 126 of the pneumostoma 110 and pushes the probe gently and slowly into the pneumostoma 110. During insertion the patient lets the probe 566 align itself with the channel 120 of the pneumostoma 110 such that when the chest mount 202 contacts and adheres to the skin 114 of the chest 100, the aperture 224 of the chest mount 202 is perfectly aligned with the aperture 126 of the pneumostoma 110. The patient then pulls gently on handle 562 to remove the alignment tool 500, leaving the chest mount 202 in place on the chest 100 of the patient ready to receive a pneumostoma vent. The alignment tool 500 is preferably formed in one piece for ease of manufacturing and safety. The pneumostoma alignment probe 566 preferably has a atraumatic tip 568 (shown in FIG. 5B) which may be soft, and or rounded so as to avoid causing injury or irritation to the pneumostoma during insertion of the probe.

Figure 5D:
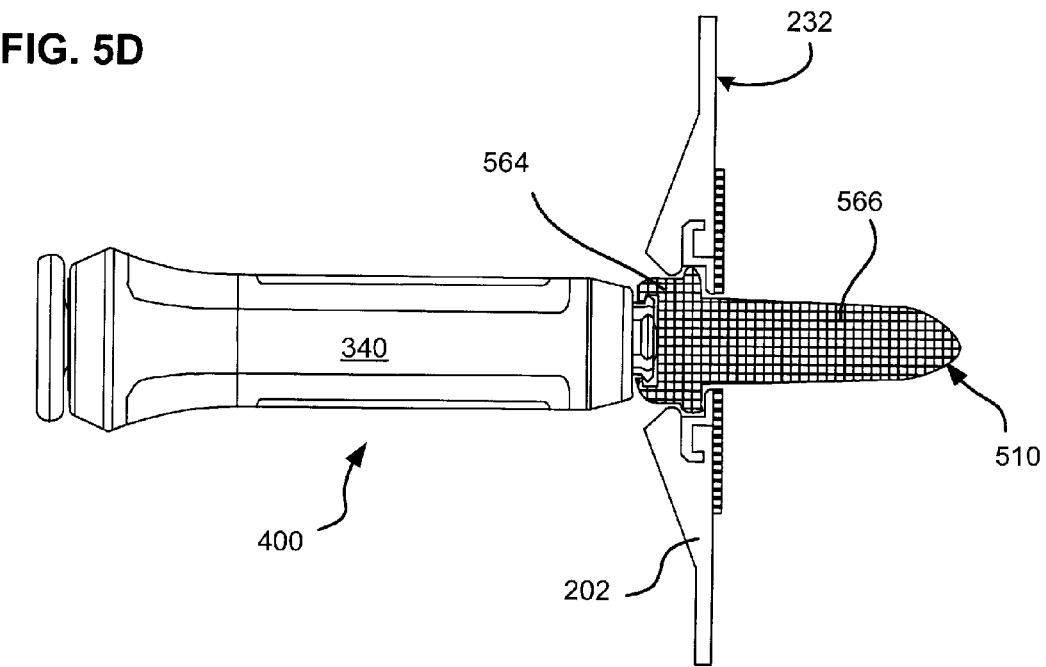

In an alternative embodiment, illustrated in FIG. 5D, an alignment tool 510 includes only the mount engagement section 564 and pneumostoma alignment probe 566. In this embodiment, the mount engagement section 564 has a recess similar to the recess in the proximal end of a pneumostoma tube for engaging a removal tool 400, as shown in FIG. 4F. The alignment tool 510 is supplied preassembled to a chest mount 202. To use this alignment tool 510, the patient first secures the removal tool 400 to the alignment tool 510. The patient then uses casing 340 or removal tool 400 to remove the chest mount 202 from its sterile packaging. The patient then removes any protective covering over the adhesive on the contact surface 232 of the chest mount 202. The patient then guides the pneumostoma alignment probe into the pneumostoma channel 120 as before. When the chest mount 202 is positioned correctly and adhered to the skin of the chest, the patient removes the removal tool 400 and pneumostoma alignment tool 500 in one piece by pulling gently on the casing 340 of the removal tool 400 leaving the chest mount in position on the chest of the patient. The patient then discards the removal tool 400 and pneumostoma alignment tool 500 locked together as one unit.

Figure 6A:
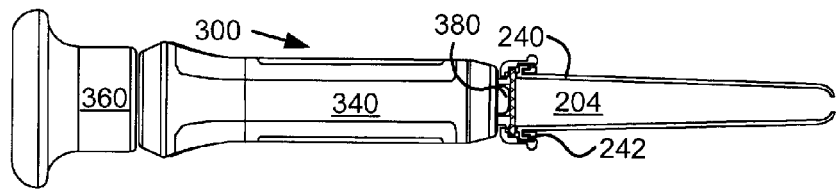
FIGS. 6A-6I show steps and tools for inserting a pneumostoma vent and removing a pneumostoma vent according to embodiments of the present invention.

FIG. 6A shows a pneumostoma vent 204 secured to an insertion tool 300. In a preferred embodiment, pneumostoma vents 204 are supplied to a patient in the configuration shown in FIG. 6A. Thus, when pneumostoma vent 204 is removed from its sterile packaging by the patient, the patient only touches insertion tool 300 by casing 340 or handle 360 and does not touch the pneumostoma vent 204 or tube 240. Note that insertion tool 300 is in the locked configuration and insertion tool 300 is securely attached to cap 242 of pneumostoma vent 204 by the grasper 380.

Figure 6B:
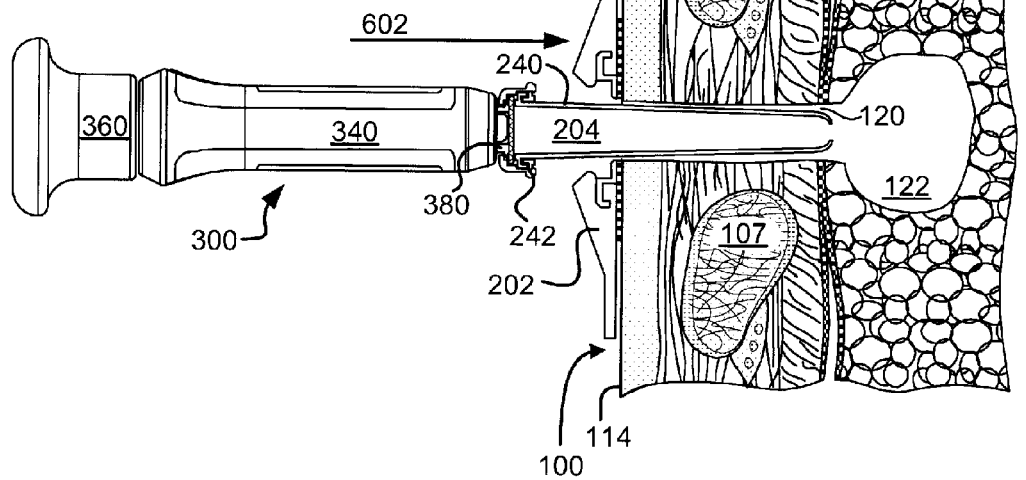
Figure 6C:
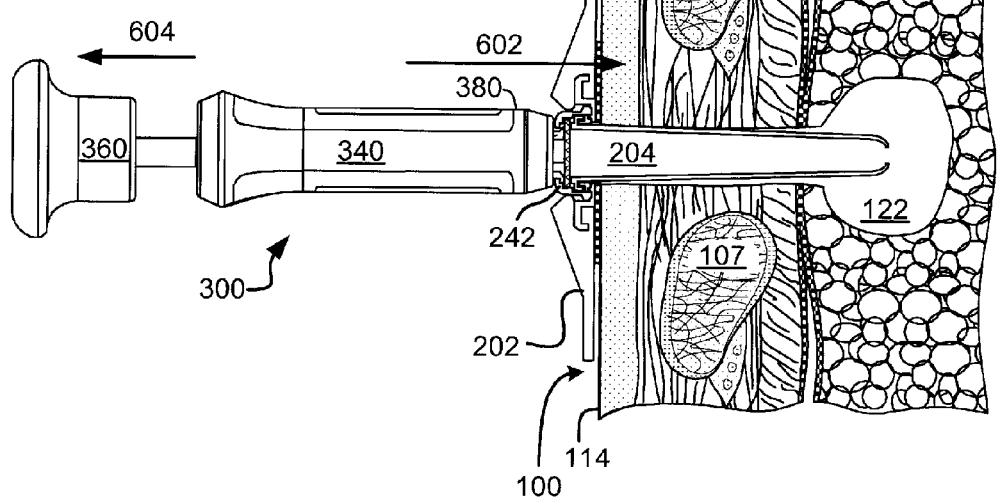
Figure 6D:
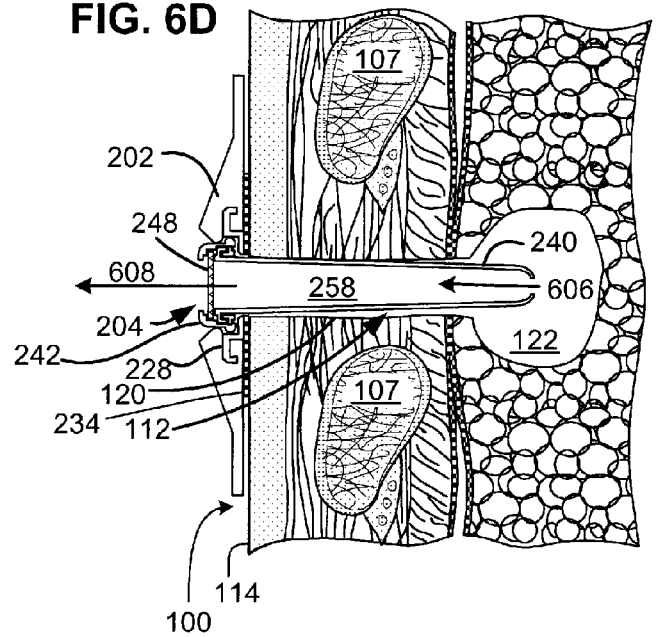

FIG. 6B shows insertion of a pneumostoma vent 204 through a chest mount 202 into a pneumostoma. The patient grips insertion tool 300 and pushes tube 240 of pneumostoma vent 204 through the aperture in chest mount 202 in the direction of arrow 602 until the cap 242 of pneumostoma vent 204 engages the chest mount 202 as shown in FIG. 6C. In this position, cap 242 is secured by chest mount 202. The patient pulls handle 360 in the direction of arrow 604. This causes insertion tool 300 to change to its unlocked configuration. In the unlocked configuration, grasper 380 releases cap 242 of pneumostoma vent 204 (See FIGS. 3D-F). This allows insertion tool 300 to be removed leaving pneumostoma vent 204 in the correct position as shown in FIG. 6D. Insertion tool 300 is now fixed in the unlocked position and may be discarded.

FIG. 6D shows a sectional view through PMD 200 and pneumostoma 110 showing the interaction of the PMD 200 with the pneumostoma 110. Tube 240 of pneumostoma vent 204 fits snugly within channel 120 of pneumostoma 110. Pneumostoma vent 204 thus maintains the patency of channel 120. Tube 240 of pneumostoma vent 204 is sized and configured such that it penetrates through channel 120 into cavity 122 in the parenchymal tissue 132 of lung 130. Chest mount 202 is secured to the skin 114 of the patient. Aperture plate 228 engages cap 242 of pneumostoma vent 204 to prevent over insertion of pneumostoma vent 204 into the pneumostoma. Adhesive 234 contacts skin 114 holding PMD 200 in position on the chest 100 of the patient. Because of the snug fit of tube 240 of pneumostoma vent 204 within channel 120 and the contact between chest mount 202 and skin 114, PMD 200 effectively controls the movement of all material (including solids, liquids and gases) in and out of the pneumostoma. Air flows from cavity 122 of pneumostoma 110 into lumen 258 of tube 240 of pneumostoma vent 204 as shown by arrow 606. From lumen 258, exhaled air flows through hydrophobic filter 248 and vents to atmosphere as shown by arrow 608.

Figure 6E:
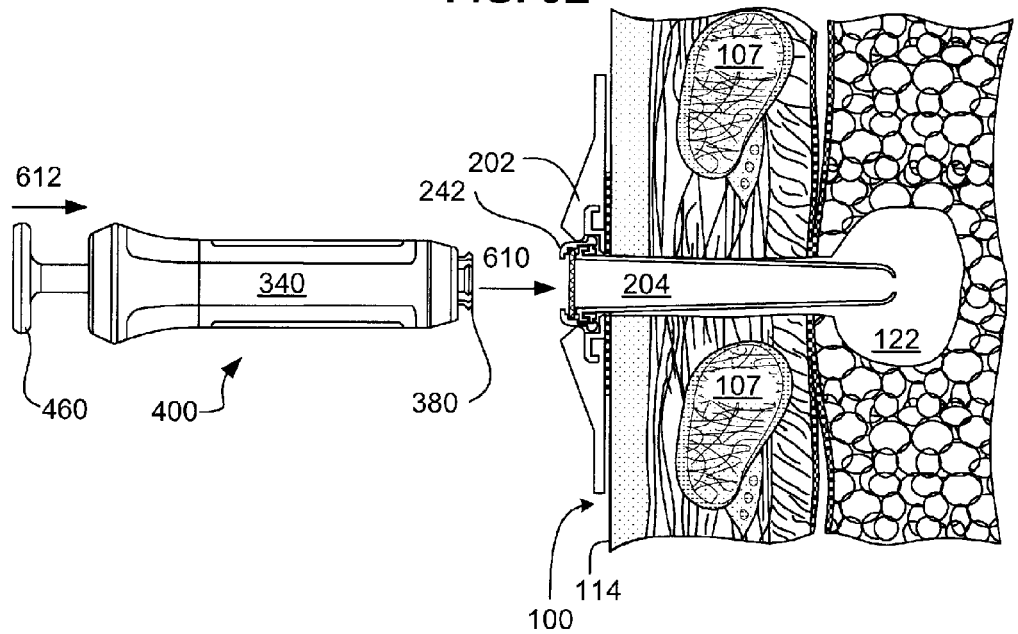
Figure 6F:
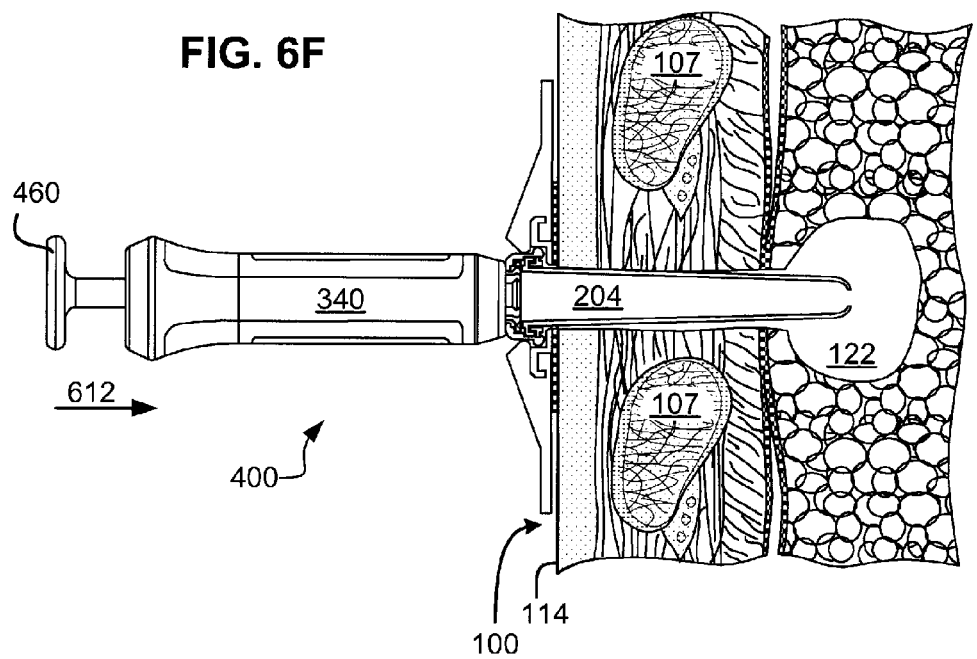
Figure 6G:
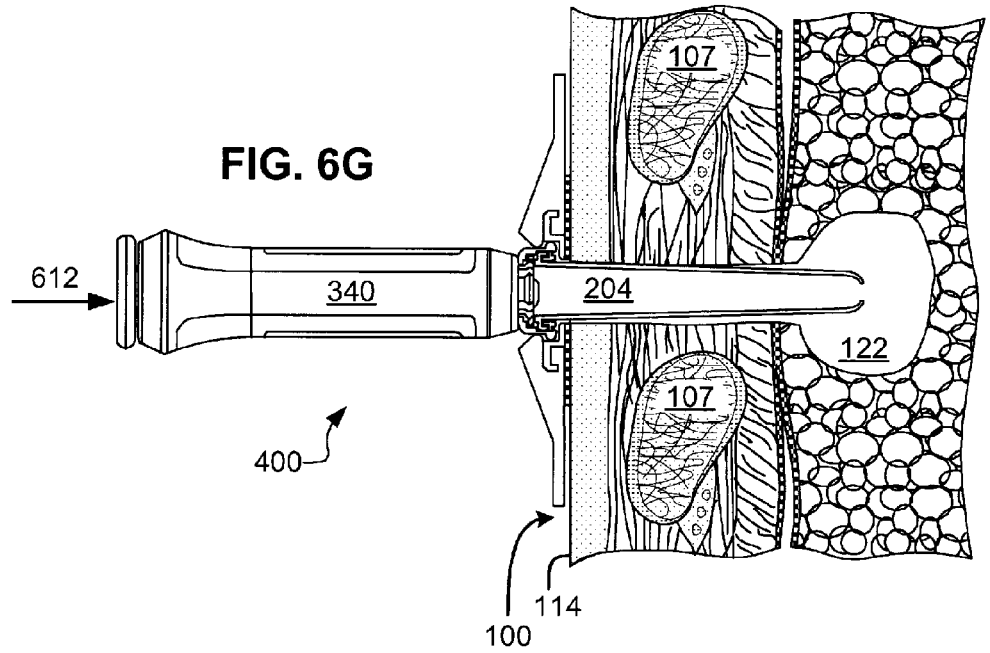

The pneumostoma vent 204 is left in position in chest mount 202. After a day (or if otherwise necessary) pneumostoma vent 204 may be removed from chest mount 202 using a removal tool 400. As shown in FIG. 6E, the patient inserts the grasper 380 of a removal tool 400 in the direction of arrow 610 into the cap 242 of the pneumostoma vent 204. When removal tool 400 is positioned as shown in FIG. 6F, the patient pushes in handle 460 in the direction shown by arrow 612. This causes removal tool 400 to change to the locked configuration in which grasper 380 is securely attached to the cap 242 of pneumostoma vent 204 as shown in FIG. 6G (see also FIGS. 4D-F).

Figure 6H:
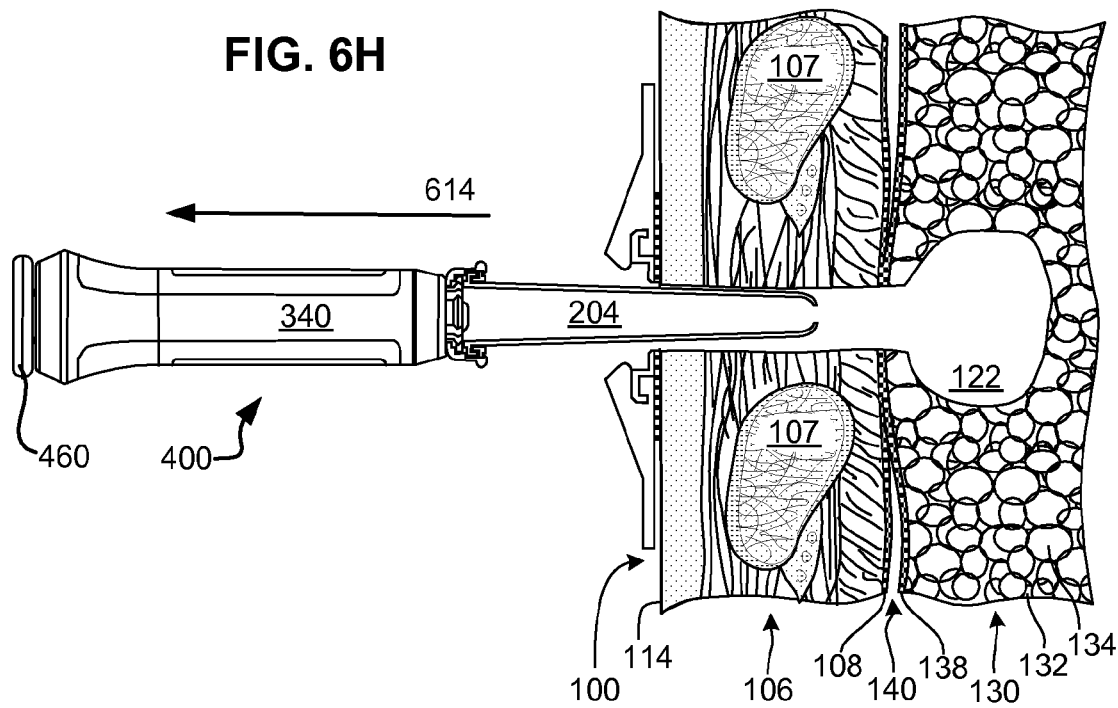
Figure 6I:
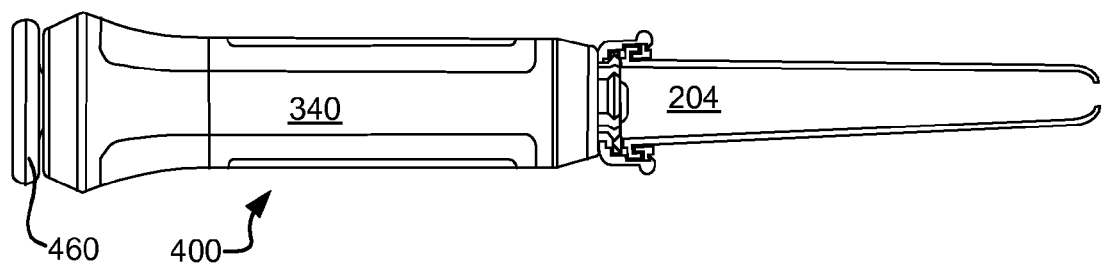

The patient may now pull casing 340 of removal tool 400 in the direction of arrow 614 as shown in FIG. 6H. Because the grasper 380 of removal tool 400 is locked to the cap 242 of pneumostoma vent 204 the pneumostoma vent 204 is removed from the chest mount 202. Pneumostoma vent 204 is removed completely from the pneumostoma and remains locked to removal tool 400 as shown in FIG. 6I. Removal tool 400 and pneumostoma vent 204 may be discarded as a single unit and a new pneumostoma vent 204 may be inserted into the pneumostoma as shown beginning with FIG. 6A.

FIG. 7A provides a set of instructions for use (IFU) 720 for replacement of a chest mount according to an embodiment of the invention. At step 722, the patient obtains the replacement chest mount and verifies that it is the correct size for his/her pneumostoma. At step 724, the patient removes the prior chest mount and disposes of it as appropriate. At step 726 the patient removes a sterile cleaning swab from the chest mount package. At step 728 the patient cleans the area of the skin around the pneumostoma. The patient cleans in a direction radially out from the pneumostoma. At step 730 the patient inspects the tissue around the pneumostoma and the pneumostoma for inflammation or injury. If injury or inflammation is observed the patient should seek medical advice.

At step 732 the patient removes a new disposable (or sterilized reusable) chest mount from its packaging. At step 734 the patient removes the backing from the adhesive pad of the chest mount. Care is taken during steps 732 and 734 to handle the chest mount only by the tabs and not to touch the surface which will be in contact with the pneumostoma. In embodiments having a pneumostoma alignment tool, the patient can handle the chest mount using the alignment tool rather than using the tabs of the chest mount. At step 736 the patient applies the chest mount to the pneumostoma aligning the aperture of the chest mount with the aperture of the pneumostoma. The chest mount may be packaged with an alignment tool to assist in positioning the chest mount correctly. If pain or injury is perceived during application the patient should seek medical advice. The steps of IFU 720 may also be performed by a caregiver or medical practitioner.

Figure 7B:
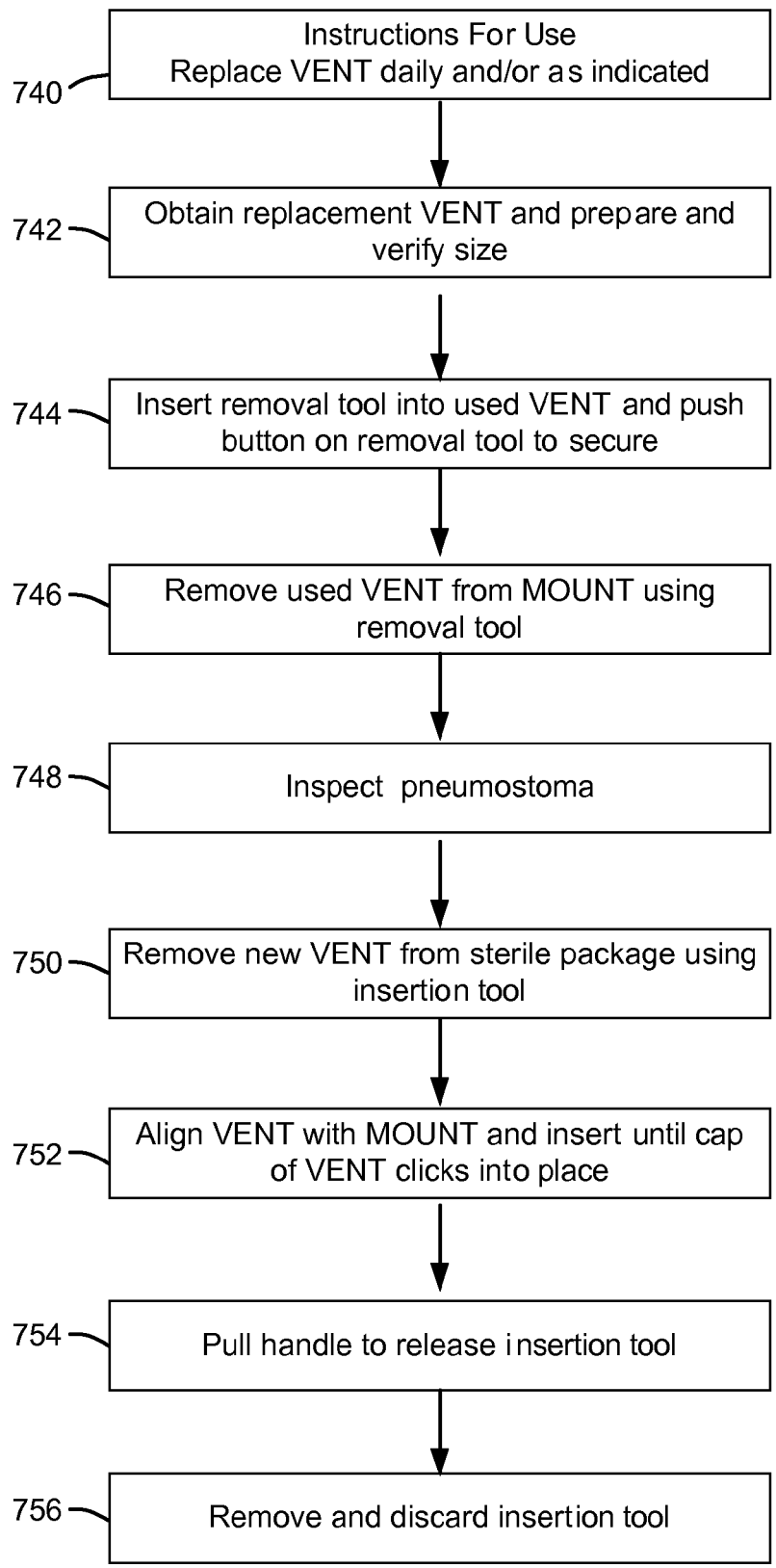

FIG. 7B provides a set of instruction for use (IFU) 740 for replacement of a pneumostoma vent according to an embodiment of the invention. At step 742, the patient obtains the replacement pneumostoma vent and verifies that it is the correct size for his/her pneumostoma. The packaging of the pneumostoma vent is clearly marked with the length of the pneumostoma vent. In addition, the pneumostoma vent can be color coded either on the cap or tube such that a particular color indicates a particular length of pneumostoma vent. At step 744, the patient takes a removal tool, inserts the grasper of the removal tool into the cap of the used pneumostoma vent and pushes in the handle to secure the removal tool to the used pneumostoma vent. At step 746 the patient removes the used pneumostoma vent by pulling on the casing of the removal tool. At step 748 the patient inspects the pneumostoma for inflammation or injury. The area around the pneumostoma and the aperture of the chest mount may be cleaned at this point if mucus or discharge is present. If injury or inflammation is observed the patient should seek medical advice.

At step 750 the patient removes a new pneumostoma vent from the packaging. Pneumostoma vent is already attached to an insertion tool so the patient does not directly touch the pneumostoma vent. The patient grips the casing of the insertion tool to install the new pneumostoma vent. At step 752 the patient aligns the tube of the new pneumostoma vent with the opening in the chest mount and inserts the pneumostoma vent using the insertion tool until the cap snaps into place. Care is taken during steps 750 and 752 to handle the pneumostoma vent only by the insertion tool and not to touch the sterile pneumostoma tube. At step 754 the patient releases the insertion tool by pulling back on the handle to cause it to enter the unlocked configuration. At step 756 the patient removes the insertion tool and discards it. If pain or injury is perceived during insertion of the pneumostoma vent the patient should seek medical advice. The steps of IFU 740 may also be performed by a caregiver or medical practitioner.

Packaging for Pneumostoma Management System

Figure 8A:
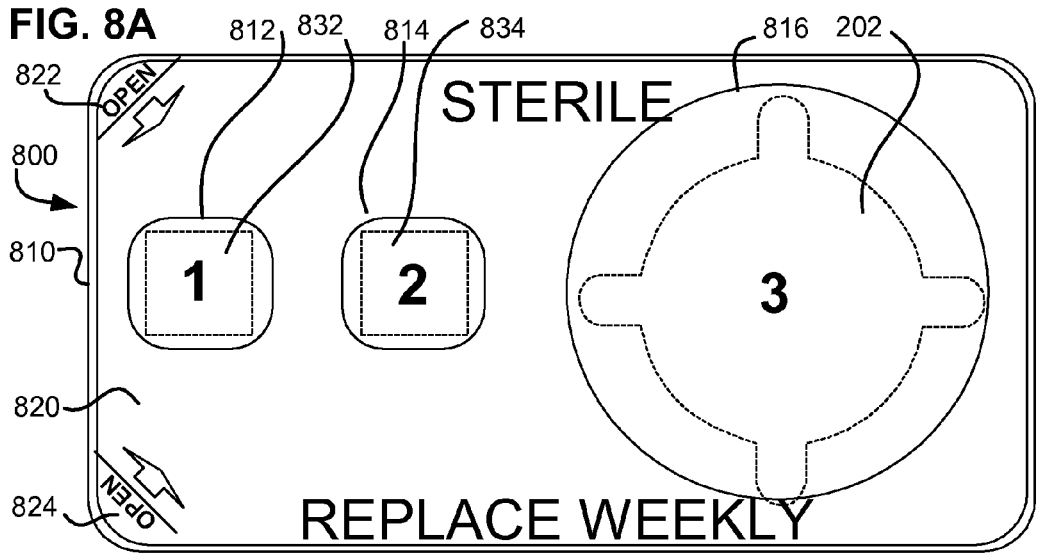
FIGS. 8A and 8B show sterile packaging for components of the pneumostoma management system in accordance with an embodiment of the present invention.
Figure 8B:
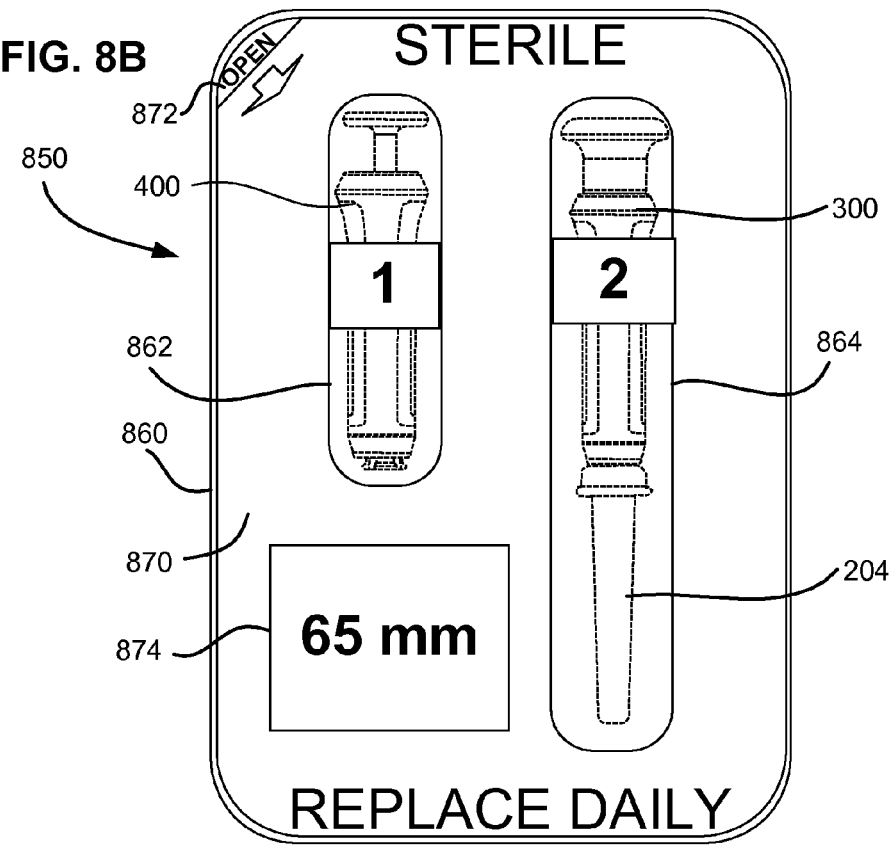

The components of the pneumostoma management system are preferably supplied to the patient in sterile packaging. In preferred embodiments, the components are supplied in packaging that assists the patient in utilizing the components of the system in the correct sequence. FIGS. 8A and 8B show an example of packaging for a chest mount 202 and a pneumostoma vent 204 respectively.

Referring now to FIG. 8A which shows package 800 for chest mount 202. Package 800 comprises a tray 810 and a top cover 820. Tray 810 comprises a plurality of dimples 812, 814, 816 sized and configured to fit the components provided in the package. In this example, dimple 812 contains a first sterile cleaning swab 832, dimple 814 contains a second sterile cleaning swab 834, and dimple 816 contains the chest mount 202. The top cover 820 is secured to the surface of tray 810 with an adhesive seal that can be broken by a patient peeling the adhesive from the opening tabs 822, 824. The top cover may be printed with material that assists the patient in the appropriate sequence of the steps for using the enclosed components. For example, a patient opening the package shown in FIG. 8A, peels top cover 820 from package 800 exposing the first sterile cleaning swab 832 for cleaning the pneumostoma, then the second sterile cleaning swab 834 for cleaning the pneumostoma, and, finally, the chest mount 202 for application to the cleaned pneumostoma. Thus, the package provides the components to the patient in the order required for use.

Referring now to FIG. 8B which shows package 850 for pneumostoma vent 204. Package 850 comprises a tray 860 and a top cover 870. Tray 860 comprises a plurality of dimples 862, 864 sized and configured to fit the components provided in the package. In this example, dimple 862 contains a removal tool 400, and dimple 864 contains an insertion tool 300 assembled to a 65 mm pneumostoma vent 204. The top cover 870 is secured to the surface of tray 860 with an adhesive seal that can be broken by a patient pealing the adhesive from opening tabs 872, 874. The top cover may be printed with material that assists the patient in the appropriate sequence of the steps for using the enclosed components. For example, a patient opening the package shown in FIG. 8A, peels top cover 870 from package 800 exposing removal tool 400 for removing the pneumostoma vent 204 to be replaced. The patient then exposes the insertion tool 300 and pneumostoma vent 204. Thus, the package provides the components to the patient in the order required for use. Additionally, the insertion tool 300 is made accessible to the patient so that the patient does not handle pneumostoma vent 204 directly. Note that the top cover is clearly marked with a size indicator 874 so that the patient may confirm that pneumostoma vent 204 is the correct size for their pneumostoma prior to commencing the replacement procedure.

As previously noted, it may be desirable to replace the chest mount 202 only every few days so as to avoid unnecessary irritation to the skin surrounding the pneumostoma. It may be desirable to replace the pneumostoma vent 204 every day. Thus, chest mount 202 is preferably provided in a separate sterile tray from the pneumostoma vent 204. In preferred embodiments a weekly kit may be provided having one chest mount 204 and seven pneumostoma vents 204. Thus, a weekly kit may be a single package including one of package 800 of FIG. 8A and seven of package 850 of FIG. 8B. Alternatively, the components may be provided as individual components separately packaged. For example, cleaning and moisturizing swabs may alternatively or additionally be packaged separately and provided to the patient. The insertion tool, removal tool and pneumostoma vent may also be separately packaged.

Additional and Alternative Pneumostoma Management Device Features

It is not necessary that a flow-control device be used in a pneumostoma vent to form an airtight seal against the entry of air into the lung through the pneumostoma. Indeed, air may enter the lung through the pneumostoma between removal and reinsertion of the pneumostoma vent 204. The pleurodesis of the pneumostoma prevents the entry of air into the pleural cavity which would otherwise cause pneumothorax. However, it is sometimes desirable to restrict flow of air in through the pneumostoma so as to encourage a reduction in hyperinflation and to preclude the aspiration of solid, liquid or gas into the lung through the pneumostoma. Thus, in alternative embodiments a pneumostoma vent may be provided with a flow control device instead of, or in addition to, the hydrophobic filter 248. The flow-control device may comprise a one-way valve assembly such as a flapper valve, Heimlich valve, reed valve or the like for allowing air to be exhaled with very low resistance through the pneumostoma while restricting the flow of air or other matter into the pneumostoma from outside the body. A suitable flow-control device preferably includes only a small number of components for ease of manufacturing and reliability and should be designed such that it has no small parts which might be aspirated through the pneumostoma.

FIGS. 9A and 9B show the cap of a pneumostoma vent 910 which includes an integrated flow control device and hydrophobic filter. Pneumostoma vent 910 includes tube 912, cap 914, snap ring 916 and filter/valve plate 918. Tube 912 has an aperture 913 which is aligned with a non-porous region 917 of the filter/valve plate 918. Filter/valve plate 918 is free to move slightly within the cap 914 in response to air pressure. As shown in FIG. 9A, when the air pressure in tube 912 is higher than the air pressure outside of cap 914 the filter/valve plate 918 moves away from tube 912 and aperture 913, thus allowing air to pass out of tube 912 and through the porous hydrophobic filter region 919 of filter/valve plate 918 along path 908. As shown in FIG. 9B, when the air pressure outside cap 914 is higher than the air pressure inside tube 912 the filter/valve plate 918 moves towards tube 912 and aperture 913, thus blocking aperture 913 with non-porous region 917 of the filter/valve plate 918 and preventing air from entering tube 913 through the cap 914. Thus, the integrated flow control device and hydrophobic filter allows air to exit pneumostoma vent 910 via the filter but operates as a one-way valve to prevent entry of air through the pneumostoma vent 910. Note also that, as before, all parts of the cap and integrated valve/hydrophobic filter are too large to fit though the aperture of a chest mount to be used with the pneumostoma vent 910 thereby precluding any failure mode in which a part of the pneumostoma vent is aspirated into the lung.

Optionally, the filter/valve plate 918 if FIGS. 9A and 9B may be biased closed with a light spring force that pushes the plate into the closed position of FIG. 9B. The spring force is selected so that it is readily overcome by the exhalation air pressure allowing the filter/valve plate 918 to move to the position shown in FIG. 9A during exhalation. In an alternative embodiment, filter/valve plate 918 may be a flexible disc that is fixed at the edges. During exhalation the center of filter/valve plate 918 bows outwards away from aperture 913 allowing the escape of air. During inhalation, the external air pressure pushes filter/valve plate 918 flat against aperture 913, thus blocking aperture 913 with non-porous region 917 of the filter/valve plate 918 and preventing air from entering tube 912 through the cap.

FIG. 9C shows an alternative pneumostoma vent 920 which has features within tube 922 designed to encourage migration of discharge such as mucus and sputum out of the lung and prevent it from re-entering the lung. These features may include barbs/fins that preferentially allow discharge to travel along and out of the inner lumen of the tube. As shown in FIG. 9C, the interior surface of tube 922 is covered with an array of barbs 925 which point away from the aperture 923 in the tube 922. Mucus and sputum that enter tube 922 through aperture 923 is pushed towards cap 924 by air flow during exhalation. When the patient inhales, some air may enter through cap 924 however the mucus and sputum is inhibited from traveling back towards aperture 923 by the shape of the barbs. Thus discharge is collected in tube 922. The discharge is removed and disposed of when pneumostoma vent 920 is replaced. Also shown in FIG. 9C, are external feature 927 such as rings or ridges which may be utilized on a pneumostoma vent to make a better seal between the exterior of the pneumostoma vent and the interior of the channel of the pneumostoma.

FIG. 9D shows an alternative pneumostoma vent 930 which has a plurality of side apertures 935 in order to facilitate entry of gases and/or discharge from a pneumostoma into the lumen 938 of tube 932. One or more side openings/apertures 935 may be provided along tube 932 and/or close to the distal tip 934. The side openings 935 may be provided instead of, or in addition to, the opening 933 in the end of distal tip 934. The side openings 935 permit gases and/or discharge to enter lumen 938 even if one or more openings is occluded by tissue or other matter.

The tube of a pneumostoma vent such as tube 932 may be created from a porous material such that air may enter the lumen of the tube through the wall of the tube. The porous tube wall may be provided in addition to, or instead of, the presence of distal opening 933 or side opening 935. The tube of pneumostoma vent, such as tube 932, may also be provided with features for maintaining the patency of the pneumostoma as shown in U.S. patent application Ser. No. 12/030,006, now U.S. Pat. No. 8,062,315, entitled "Variable Parietal/Visceral Pleural Coupling" which is incorporated herein by reference.

Figure 9E:
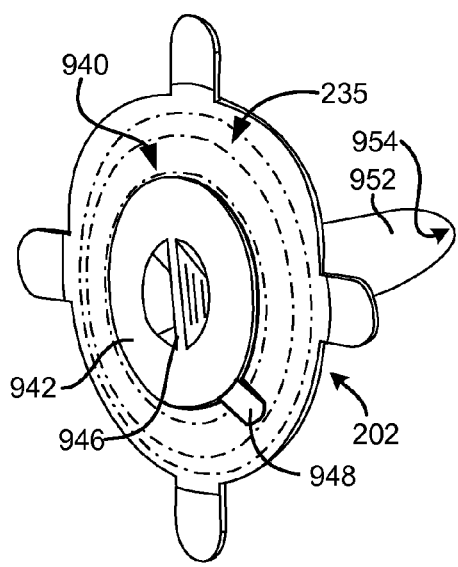
FIGS. 9E-9H show pneumostoma plugs according to embodiments of the present invention.
Figure 9F:
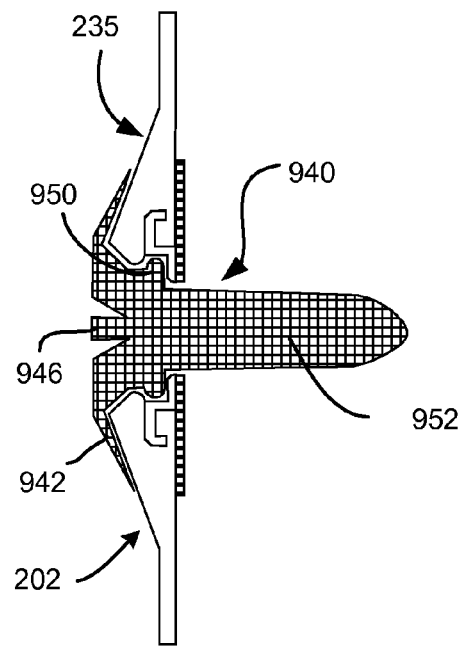
Figure 9G:
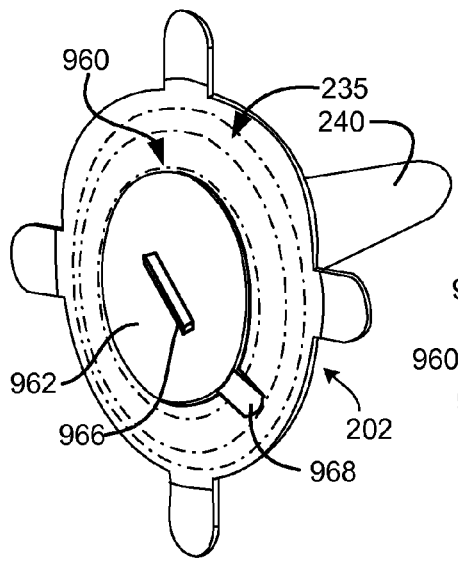

FIGS. 9E and 9F show views of a pneumostoma plug 940 which may be used to protect the pneumostoma from the entry of foreign material during times or activities when a pneumostoma vent is not present in chest mount 202. Or when it is necessary or desirable to close the pneumostoma for activities such as, for example, spirometry testing of lung function or swimming. As shown in FIG. 9E, pneumostoma plug 940 includes a cover 942 for covering the external aperture in chest mount 202. The cover 942 preferably conforms to the outside surface 235 of chest mount 202 to form a functional seal of the aperture. If the exterior surface of cover 942 is subjected to increased pressure, such as by water pressure when swimming, cover 942 is pushed into better contact with surface 235 making a better seal and precluding the entry of water.

Pneumostoma plug 940 has a recessed handle 946 or similar gripping mechanism to allow plug 940 to be grasped by the patient and removed from chest mount 202 when necessary. One or more tabs 948 may be provided on the periphery of cover 942 to allow the cover to be grasped by the patient to remove pneumostoma plug 940. Tabs 948 may be provided instead of, or in addition to, handle 946. Plug 940 is, however, preferably low profile so as to avoid being caught and removed accidentally during an activity.

Below cover 942 is a chest mount engagement section 950 (shown in FIG. 9F) which is shaped similarly to the cap of a pneumostoma vent in order to engage the recess of the chest mount. Chest mount engagement section 950 ensures that pneumostoma plug 940 snaps into place in chest mount 202 and remains there until removed by patient. Note that cover 942 and chest mount engagement section 950 are large enough to preclude pneumostoma plug 940 from passing through the aperture of the chest mount 202.

The only region of pneumostoma plug 940 that can pass through the aperture of the chest mount is stopple 952. Stopple 952 is sized and configured to penetrate through the aperture into the pneumostoma and to fill the pneumostoma tightly so as to prevent the entry or exit of material through the pneumostoma. Stopple 952 preferably has an atraumatic tip 954 which is soft, and or curved to facilitate insertion of stopple 952 and reduce irritation to the pneumostoma. Note that stopple 952 is relatively short compared to a pneumostoma vent such that stopple 952 preferably does not penetrate beyond the end of channel of pneumostoma. Stopple 952 preferably does not penetrate into the cavity so as to preclude contact of stopple 952 with lung parenchymal tissue during vigorous activity. The surface of stopple 952 may also be provided with surface features such as ridges (not shown) to make a better seal of the pneumostoma.

Figure 9H:
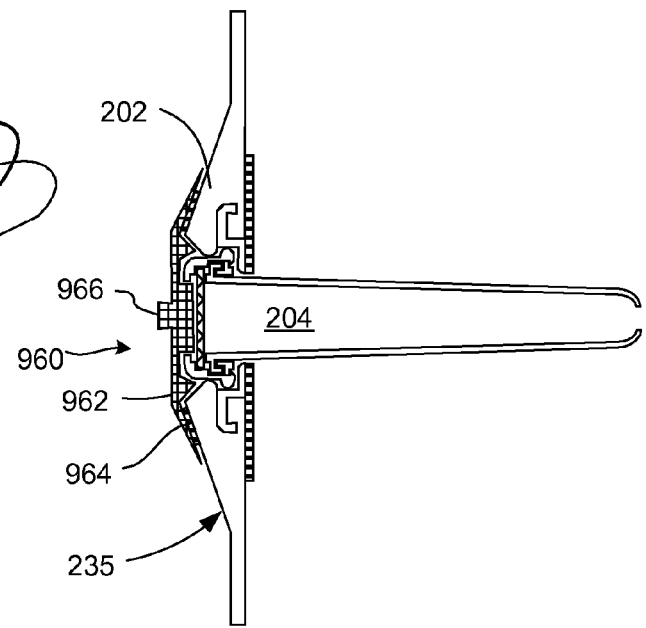

FIGS. 9F and 9H illustrate an alternative pneumostoma plug 960 designed to operate in conjunction with a pneumostoma vent 204. Pneumostoma plug 960 comprises a cover 962 designed to engage the top surface 235 of a chest mount 202. Note that pneumostoma plug 960 is designed such that it will not fit through the aperture of chest mount 202 even if pneumostoma vent 204 is absent. Pneumostoma plug 960 is provided with a ring of releasable adhesive 964 to secure it to the top surface 235 of chest mount 202. Pneumostoma plug is provided with a handle 966 or tab 968 to facilitate application or removal of pneumostoma plug 960. Pneumostoma plug 960 is designed to fill the portion of the recess of chest mount 202 not filled by pneumostoma vent 204. Unlike the pneumostoma plug 940 of FIGS. 9E-9F, pneumostoma plug 960 does not include a stopple 952. During use of plug 960, the channel of a pneumostoma will contain the tube 240 or pneumostoma vent 204. Pneumostoma plug 960 is non-porous and may be used to temporarily cover and/or seal a pneumostoma vent 204 during brief activities such as e.g. spirometry testing, showering or working in a dirty environment.

FIGS. 10A-D illustrate alternative configurations of adhesive on the contact surface 232 of a chest mount 1020, 1040, 1050. Flanges 222 of each chest mount 1020, 1040, 1050 have adhesive material distributed thereon. Adhesive materials may be hydrocolloid adhesives which absorb moisture while retaining good adhesiveness. However, even the best adhesives may cause irritation of the skin during prolonged exposure. Tissue irritation may result merely from build up of moisture on the skin behind PMD 200 regardless of the presence of any particular adhesive. However, the distribution of adhesive may be controlled so as to help reduce irritation to the skin of the patient. One way to achieve this is by reducing the amount of time any particular portion of skin is in contact with adhesive and/or allowing the skin in regions behind PMD 200 to "breathe" when not in contact with adhesive. Thus, in some embodiments the adhesive may be provided in stripes or patches and absent in other stripes or patches. The adhesive areas may also be elevated slightly above the surface of flange 222 such that non adhesive areas of flange 222 do not contact the skin but leave a slight air gap through which air may circulate and/or moisture may escape. The adhesive patches themselves may comprise a breathable laminate and adhesive so that the prolonged attachment of the PMD does not irritate the skin. Furthermore, a chest mount may be provided with one or more tabs which are free of adhesive. These tabs allow a patient to get a purchase on the chest mount to gently peel the chest mount off the skin when it needs replacement. The adhesive patches may be arranged differently on different chest mounts so as to contact different regions of skin surrounding a pneumostoma. Alternatively, the arrangement of adhesive patches may be the same on each chest mount but the registration of the patches may be changed by chance or deliberately each time a chest mount is replaced so that the adhesive patches contact different regions of skin surrounding a pneumostoma.

Referring now to FIG. 10A where the contact surface 232 of a flange 222 of a chest mount 1020 is shown. Adhesive pads 1034, 1035 are located on contact surface 232 around aperture 224. The adhesive is selected so as to help maintain the correct position of chest mount 1020 without causing undue irritation to the skin of the patient. As shown in FIG. 10A, adhesive pads 1034, 1035 are provided in two discrete spaced-apart regions. Each adhesive pad 1034, 1035 preferably comprises a laminate structure with an inner plastic, paper or foam layer (e.g., closed-cell polyethylene foam) sandwiched between layers of adhesive. The adhesive pads 1034, 1035 are elevated above contact surface 232 by the thickness of the inner layer. Thus, only some portions of skin around a pneumostoma will be in contact with adhesive each time chest mount 1020 is changed. Different chest mounts may be provided with different arrangements of adhesive patches. For example, a second chest mount may have adhesive patches located in the empty areas 1036, 1037 of contact surface 232 such that it will contact different areas of skin. FIG. 10B shows a sectional view of chest mount 1020 along line B-B. FIG. 10B shows that contact surface 232 is spaced apart from the skin of the patient when chest mount 1020 is applied around aperture 224. Air can circulate between the adhesive pads 1034, 1035. As previously described, the adhesive pads may be protected by a protector sheet that is removed prior to use of PMD 200.

Any medically approved water resistant pressure sensitive adhesive may be used to attach the chest mount to the skin of the patient, such as hydrocolloid adhesives, zinc oxide adhesives and hydrogel adhesives. Particularly effective adhesives in providing the desired adhesive properties to secure the chest mount to the skin of the wearer without irritation are formed from cross-linking polymers with a plasticizer to form a 3-dimensional matrix. Some useful adhesives are disclosed in WO 00/07637, WO 00/45866 WO 00/45766 and U.S. Pat. No. 5,543,151 which are incorporated herein by reference. The adhesive can be applied to the contact surface 232 of flange 222 by any means known in the art such as slot coating, spiral, or bead application or printing.

Referring now to FIG. 10C where a different distribution of adhesive on contact surface 232 of a chest mount 1040 is shown. As shown in FIG. 10C, adhesive pads may be distributed in small patches 1042. The adhesive patches 1042 may cover a less than 100% of the contact area 232. As shown in FIG. 10C, adhesive patches 1042 cover approximately half of the contact surface 232 of chest mount 1040. Adhesive patches preferably cover from 10% to 50% of contact surface 232. With the distribution pattern of FIG. 10C, all chest mounts may have the same distribution of adhesive. Because patches 1042 are small and evenly distributed, variations of the orientation of placement of chest mount 1040 will randomize the location of the patches 1042 relative to the skin of the patient such that a particular region of skin is only in contact with adhesive for a percentage of time similar to the percentage of coverage.

FIG. 10D illustrates an alternative method for rotating the portions of skin around a pneumostoma that are in contact with adhesive. As shown in FIG. 10D, chest mount 1050 has eight radial adhesive patches 1052. The patches are arranged in a regular pattern such that the patches are interspersed with non-adhesive areas 1054. As shown in FIG. 10D, adhesive patches 1052 cover approximately half of the contact surface 232 of chest mount 1050. Adhesive patches preferably cover from 10% to 50% of contact surface 232. A tab 236 is aligned with one of the adhesive patches 1052. With the chest mount 1050 of FIG. 10D, the patient deliberately changes the orientation of tab 236 relative to the pneumostoma each time a chest mount is changed. By changing the rotation of the chest mount 1050 the patient can change which portions of skin are in contact with adhesive patches 1052.

The functional purpose of the chest mount is: providing an aperture; positioning the aperture in alignment with a pneumostoma; providing a contact surface with which to secure the chest mount to the patient; and providing a coupling to releasably receive a pneumostoma vent and secure the pneumostoma vent through the aperture into the pneumostoma. Thus, different designs of chest mount 1060 may be made without departing from the scope of the invention. FIG. 10E illustrates an alternative design of a chest mount 1060. Chest mount 1060 is formed in one piece and does not comprise separate flange 222 and aperture plate 228 components. As all the components of chest mount 1060 are made from the same material, the desired mechanical properties of portions of chest mount 1060 are achieved by changing design parameters. For example, the desired conformability is achieved in the flange region 1062 of chest mount 1060 by reducing the thickness of the material. Cavity 1064 allows for a reduced thickness of material while maintaining the overall shape of chest mount 1060. The material of chest mount 1060 is also thicker in region 1066 in the vicinity of aperture 224 so as to make the material around aperture 224 stiffer in order to control the dimensions of aperture 224.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A medical device used to allow gases to exit a lung of a patient through a pneumostoma in a chest, wherein the medical device comprises;
   a vent adapted to be inserted into the chest through the pneumostoma to permit gases to exit a lung of the patient through the pneumostoma via the vent, wherein the vent includes,
      a distal opening in a distal end of the vent adapted to admit gases from the lung,
      a proximal opening in a proximal end of the vent adapted to allow gases from the lung to exit the vent outside of the chest of the patient, and
      a tubular body adapted to slide into the pneumostoma and sized so as to place the distal end of the vent within the lung while the proximal end of the vent is external to the chest; and
   a chest mount having an adhesive surface adapted to releasably secure the chest mount to the chest of the patient, wherein the chest mount includes,
   an aperture through the chest mount, which aperture is stiff and less compliant than a flange of the chest mount;
   said flange having the adhesive surface for releasably securing the chest mount to the chest of the patient wherein the flange is thin, elastic, flexible and compliant so that it is adapted to conform to the chest of the patient; and
   whereby the distal end of the vent is adapted to be selectively positioned within the parenchymal tissue of the lung, while the proximal end of the vent communicates with the aperture.

2. The medical device of claim 1, wherein the aperture passes centrally through the chest mount.

3. The medical device of claim 1, wherein the vent comprises a cap connected to the proximal end of the tubular body and wherein the cap includes a filter.

4. The medical device of claim 1, wherein the vent comprises a cap connected to the proximal end of the tubular body wherein each component of the cap is too large to pass completely through the aperture such that the aperture prevents each component of the cap from passing into the pneumostoma.

5. The medical device of claim 1, wherein the vent comprises a cap connected to the proximal end of the tubular body wherein the cap includes a filter and wherein each component of the cap, including the filter, is too large to pass completely through the aperture such that the aperture prevents each component of the vent cap from passing into the pneumostoma.

6. The medical device of claim 1, wherein the chest mount includes a recess adjacent the aperture and the proximal end of the vent fits within the recess such that it is substantially flush with the chest mount when the vent is positioned in the pneumostoma.

7. The medical device of claim 1, wherein the vent comprises a cap connected to the proximal end of the tubular body and wherein the proximal end of the tubular body is larger than the diameter of the aperture so that the aperture prevents the proximal end of the tubular body from passing into the pneumostoma.

8. The medical device of claim 1, wherein the vent is removably secured to the chest mount and the chest mount is adapted to remain secured to the chest of the patient when the vent is removed.

9. The medical device of claim 1, wherein the vent is flush with the chest mount.

10. The medical device of claim 1, wherein the chest mount is adapted to be secured to a patient for about a week before being replaced.

11. The medical device of claim 1, wherein the vent is secured to the chest mount for about a day before being replaced.

12. The medical device of claim 1, wherein the chest mount is conical in shape.

13. The medical device of claim 1, wherein the chest mount is substantially flush with the skin of a patient.

14. The medical device of claim 1, wherein the chest mount is dome shaped.

15. A medical device used to allow gases to exit a lung of a patient through a passage which passes through a chest wall into the lung through a region of pleurodesis between visceral and parietal membranes surrounding the lung, wherein the medical device comprises;
    a chest mount which comprises,
        an adhesive surface adapted to releasably secure the chest mount to the chest of the patient;
        an aperture through the chest mount, which aperture is stiffer and less compliant than a flange of the chest mount; and
        said flange having the adhesive surface for releasably securing the chest mount to the chest of the patient wherein the flange is thin, elastic, flexible and compliant so that it is adapted to conform to the chest of the patient; and
    a vent adapted to be inserted into the chest through the passage which passes through the chest wall into the parenchymal tissue of the lung to permit gases to exit a lung of the patient, wherein the vent comprises,
        a distal opening in a distal end of the vent adapted to admit gases from the parenchymal tissue of the lung, and
        a proximal opening in a proximal end of the vent adapted to allow gases from the parenchymal tissue of the lung to exit the vent outside of the chest of the patient and;
    whereby the distal end of the vent is adapted to be selectively positioned within the parenchymal tissue of the lung while the proximal end of the vent is releasably secured to the chest mount.

16. The medical device of claim 15, wherein the aperture passes centrally through the chest mount.

17. The medical device of claim 15, wherein the vent comprises a cap connected to the proximal end of the tubular body and wherein the cap includes a filter.

18. The medical device of claim 15, wherein the vent comprises a cap connected to the proximal end of the tubular body, wherein each component of the cap is too large to pass completely through the aperture such that the aperture prevents each component of the cap from passing into the passage.

19. The medical device of claim 15, wherein the vent is flush with the chest mount.

20. The medical device of claim 15 wherein the vent is releasably secured to the chest mount.

21. A medical device used to allow gases to exist the lung of a patient through a pneumostoma in the chest, wherein the medical device comprises;
    a vent adapted to be inserted into the chest through the pneumostoma to permit gases to exit the parenchymal tissue of the lung of the patient through the pneumostoma via the vent, wherein the vent includes,
        a distal opening in a distal end of the vent adapted to admit gases from the parenchymal tissue of the lung,
        a proximal opening in a proximal end of the vent adapted to allow gases from the lung to exit the vent outside of the chest of the patient, and
        a tubular body adapted to slide into the pneumostoma and sized so as to place the distal end of the vent within the parenchymal tissue of the lung while the proximal end of the vent is external to the chest; and
    a chest mount having an adhesive surface adapted to releasably secure the chest mount to the chest of the patient, wherein the chest mount includes
    an aperture which is stiff and less compliant than a flange of the chest mount; and
    said flange having the adhesive surface releasably securing the chest mount to the chest of the patient wherein the flange is thin, flexible elastic and compliant so that it is adapted to conform to the chest of the patient; and
    whereby the distal end of the vent is substantially flush with the chest mount.

* * * * *